US 8,189,041 B2

(12) United States Patent
Konishi et al.

(10) Patent No.: US 8,189,041 B2
(45) Date of Patent: May 29, 2012

(54) ENDOSCOPE SIGNAL PROCESSING APPARATUS

(75) Inventors: Jun Konishi, Hachioji (JP); Kentaro Hase, Hachioji (JP); Tsutomu Hirai, Sagamihara (JP); Shoichi Amano, Hachioji (JP); Tomoki Iwasaki, Hino (JP); Katsuyuki Saito, Sagamihara (JP); Makoto Tsunakawa, Toda (JP); Takehiro Nakagawa, Shiojiri (JP)

(73) Assignee: Olympus Corporation, Tokyo (JP)

( * ) Notice: Subject to any disclaimer, the term of this patent is extended or adjusted under 35 U.S.C. 154(b) by 1519 days.

(21) Appl. No.: 11/701,197

(22) Filed: Feb. 1, 2007

(65) Prior Publication Data

US 2007/0139522 A1 Jun. 21, 2007

Related U.S. Application Data

(63) Continuation of application No. PCT/JP2005/013966, filed on Jul. 29, 2005.

(30) Foreign Application Priority Data

Aug. 5, 2004 (JP) ................................. 2004-229713

(51) Int. Cl.
*A62B 1/04* (2006.01)
(52) U.S. Cl. .................. 348/65; 348/71; 348/72
(58) Field of Classification Search .................. 348/169, 348/71–72, 65, 441
See application file for complete search history.

(56) References Cited

U.S. PATENT DOCUMENTS

| 6,491,628 | B1 * | 12/2002 | Kobayashi | 600/168 |
|---|---|---|---|---|
| 2003/0025830 | A1 * | 2/2003 | Perry | 348/441 |
| 2004/0080612 | A1 * | 4/2004 | Sugimoto | 348/65 |
| 2004/0085442 | A1 * | 5/2004 | Kawata | 348/65 |
| 2004/0116908 | A1 | 6/2004 | Birkenbach et al. | |
| 2005/0020879 | A1 | 1/2005 | Suzuki | |

FOREIGN PATENT DOCUMENTS

| EP | 1 512 365 A1 | 3/2005 |
|---|---|---|
| JP | 04-253831 | 9/1992 |
| JP | 06-169886 | 6/1994 |
| JP | 06-285017 | 10/1994 |
| JP | 2004-000335 | 1/2004 |
| JP | 2004-008329 | 1/2004 |
| JP | 2005-296534 | 10/2005 |
| WO | WO 03/101285 A1 | 12/2003 |

* cited by examiner

*Primary Examiner* — Abdullahi Salad
(74) *Attorney, Agent, or Firm* — Scully, Scott, Murphy & Presser, P.C.

(57) ABSTRACT

An endoscope signal processing apparatus has a first video signal generating circuit and a second video signal generating circuit which respectively generate a first video signal and a second video signal offering different resolutions depending on a first image capturing device and a second image capturing device respectively which are mounted in an endoscope removably connected to an endoscope connecting portion. The first and second video signals can be selectively output to an exterior through a common video signal output connector.

23 Claims, 21 Drawing Sheets

| P11 | P12 | P13 | P14 | P15 | P16 | P17 | P18 | P19 | ←—104 |
|-----|-----|-----|-----|-----|-----|-----|-----|-----|------|
| P21 | P22 | P23 | P24 | P25 | P26 | P27 | P28 | P29 | |
| P31 | P32 | P33 | P34 | P35 | P36 | P37 | P38 | P39 | |

Ra

4 : 3 MODE

5 : 4 MODE

| MONITOR OUTPUT | HD-OSD | SD-OSD | SELECTION BY SELECT CIRCUIT 82 | SELECTION BY SELECT CIRCUIT 84 |
|---|---|---|---|---|
| HDTV MODE | IN USE | OFF | HD-OSD | HD/SD CONVERSION |
| SDTV MODE | OFF | IN USE | SD-OSD | SD-OSD |

ENDOSCOPE SIGNAL PROCESSING APPARATUS

CROSS REFERENCE TO RELATED APPLICATION

This application is a continuation application of PCT/JP2005/013966 filed on Jul. 29, 2005 and claims benefit of Japanese Application No. 2004-229713 filed in Japan on Aug. 5, 2004, the entire contents of which are incorporated herein by this reference.

BACKGROUND OF THE INVENTION

1. Field of the Invention

The present invention relates to an endoscope signal processing apparatus that generates various video signals from image capturing signal from a solid image capturing device mounted in an endoscope.

2. Description of the Related Art

In recent years endoscope system has been prevailing widely which carries out endoscopic examinations or diagnoses by displaying on display means endoscopic images captured by image capturing means that uses a solid image capturing device.

For example, an endoscope system disclosed in Japanese Patent Laid-Open No. 6-169886 selectively can display an endoscopic image and a video image from an external instrument such as a VTR, a video printer, or an image filing apparatus, on a monitor.

The endoscope system has plural terminals through which plural types of video signals (specifically, RGB signals, S/Y separation video signals, and composite video signals) from a video processor are input to the monitor. Simply operating the video processor allows any video signals to be input to the monitor.

Japanese Patent Laid Open No. 2004-335 discloses an endoscope system that can output two types of video signals, SDTV (Standard Definition Television) video signals and HDTV (High Definition Television) video signals such as high vision video signals. A video processor in this system can output SDTV video signals and HDTV video signals from an SDTV connector and an HDTV connector, respectively.

The SDTV signals involve an RGB signal format, a YPbPr signal format, and a composite signal format. RGB signals have been conventionally used to observe endoscopic images.

On the other hand, the HDTV signals involve the RGB signal format and a YPbPr signal format, and YPbBr signals are mainly used.

SUMMARY OF THE INVENTION

An endoscope signal processing apparatus in accordance with the present invention comprises: an endoscope connecting portion to which an endoscope is removably connected; a first video signal generating circuit for generating a first video signal in association with a first image capturing device mounted in the endoscope connected to the endoscope connecting portion; a second video signal generating circuit for generating a second video signal in association with a second image capturing device mounted in the endoscope connected to the endoscope connecting portion, the second video signal offering a resolution different from that of the first video signal; and a common video signal output connector that selectively outputs the first video signal and the second video signal to an exterior.

BRIEF DESCRIPTION OF THE DRAWINGS

FIG. 11 is a diagram of an example of an image zoom-in display in accordance with a variation that is different from FIG. 10B and the like;

DETAILED DESCRIPTION OF THE PREFERRED EMBODIMENT(S)

Figure 1:
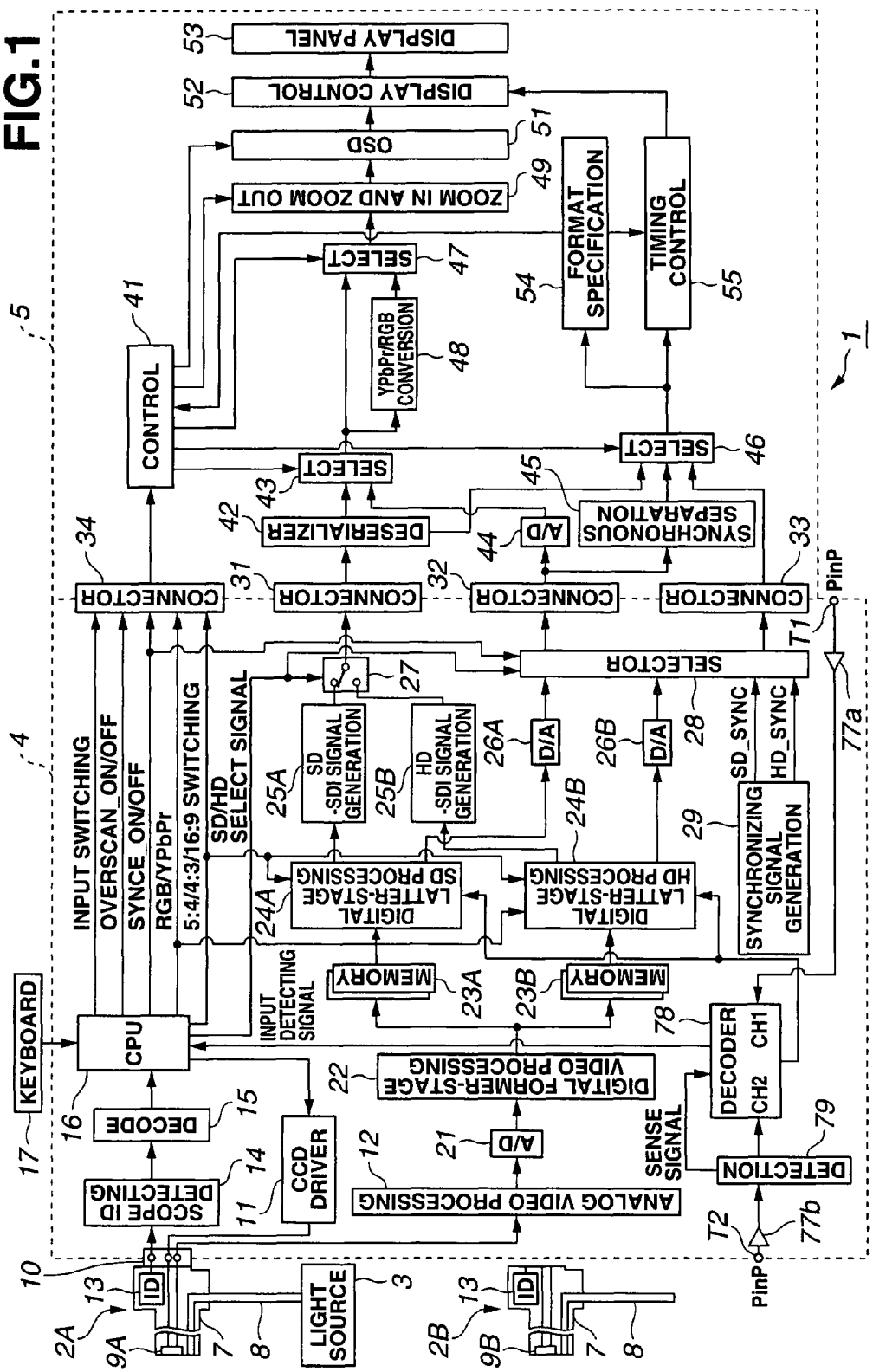
FIG. 1 is a block diagram showing the general configuration of an endoscope system according to Embodiment 1 of the present invention.

An embodiment of the present invention will be described below with reference to the drawings.

Embodiment 1

Embodiment 1 of the present invention will be described with reference to FIGS. 1 to 21.

An endoscope system 1 shown in FIG. 1 comprises endoscopes (hereinafter simply referred to as scopes) 2A, 2B which are inserted into a body cavity to execute endoscopic examinations, a light source device 3 that supplies illumination light to a scope 2I (I=A, B), a video processor having a signal connector receiver 10 to which a signal connector of the scope 2I is removably connected, the video processor 4 serving as a endoscope signal processing apparatus to process signals with respect to image capturing means mounted in the scope 2I, and a monitor 5 to which video signals are input via the connector removably connected to the video processor 4 to display endoscopic images captured by the image capturing means.

In the present embodiment, the scope 2I has various CCDs 9I mounted therein. Accordingly, the video processor 4 to which the scope 2I is removably connected can execute signal processes corresponding to the respective CCD 9I. That is, in FIG. 1, the scope 2A is connected to the video processor 4. However, the different scope 2B is connected to the video processor 4; the scope 2B has a CCD 9B mounted therein and having a pixel count (resolution) and the like which are different from those of a CCD 9A mounted in the scope 2A.

The CCDs 9A and 9B in this example typically have pixel counts corresponding to SDTV (Standard TV) video signals and higher-definition TV video signals, for example, high vision video signals (High Definition Television is hereinafter simply referred to as HDTV). For simplification, SDTV or an SDTV video signal is hereinafter simply referred to as SDTV. HDTV or an HDTV video signal is hereinafter simply referred to as HDTV.

The video processor 4 comprises a function for executing a signal process of generating SDTVs and a signal process of generating HDTVs depending on the CCD 9I mounted in the scope 2I. In variations described below, the video processor 4 may comprise a function for converting HDTVs into SDTVs and outputting the SDTVs for the HDTV-compatible CCD 9B.

Further, in association with the video processor 4, comprising the signal processing function for generating SDTVs and HDTVs, the monitor 5 comprises a function for performing display operations compatible with both SDTV and HDTV signal formats.

In this case, the present embodiment enables both SDTV and HDTV video signals offering different resolutions to be selectively output to the monitor 5 through common connectors 31, 32. This facilitates connection operations to improve operability and saves required spaces.

Further, a user can input an instruction for a signal format or the like via a keyboard 17 to allow a remote signal corresponding to the instruction input serving as control information to be sent from the video processor 4 to the monitor 5. This enables a display process on the monitor 5 to be remotely controlled in accordance with the instruction input as described below.

The scope 2I has an elongate insert portion 7 that is inserted into the body cavity and a light guide 8 placed in the insert portion 7 to transmit illumination light. Illumination light from the light source device 3 is incident on an incident end surface at a rear end of the light guide 8. The light guide 8 transmits the incident illumination light and emits it from a distal end surface attached to an illumination window at a distal end of the insert portion 7. This allows a subject such as a diseased part to be illuminated.

An objective lens (not shown) is attached to an observation window provided adjacent to the illumination window. The objective lens has a solid image capturing device, for example, a charge coupled device (hereinafter referred to as a CCD), placed at its position where an image is formed. The CCD 9I photoelectrically converts an optical image formed on its image capturing surface. The CCD 9I contained in the scope 2I comprises CCDs compatible with SDTVs and HDTVs, respectively. Alternatively, video signals for an image obtained by the CCD 9I may be superimposed on some of the SDTV and HDTV video signals, so that the CCD can deal with both SDTVs and HDTVs.

The signal connector of the scope 2I is connected to the signal connector receiver 10 of the video processor 4 to allow the CCD driver 11 provided in the video processor 4 to apply a CCD drive signal to the CCD 9. The CCD 9 outputs a CCD output signal resulting from a photoelectric conversion associated with the application of the CCD drive signal, to an analog video processing circuit 12 in the video processor 4.

Each scope 2I contains a scope ID generating circuit (in FIG. 1, simply referred to as an ID) 13 that generates an ID code inherent in the scope 2I. The scope ID code is read by a scope ID detecting circuit 14 in the video processor 4 and decoded via a decode circuit 15. The decoded information is then input to a CPU 16 that controls the sections in the video processor 4.

In accordance with ID codes and instruction inputs from the keyboard 17, the CPU 16 controllably drives the CCD driver 11 that drives the CCD 9I contained in the scope 2I, and controls the section of a signal processing system that processes CCD output signals. If the scope does not have the scope ID generating circuit 13, a process for the CCD 9I contained in the scope can be instructively set via the keyboard 17 provided outside the video processor 4. The keyboard 17 is connected to the CPU 16 inside the video processor 4. The user can thus input patient information via the keyboard 17 for endoscopic examinations or input control commands for the CPU 16 to control the sections in the video processor 4. Further, in addition to controlling the sections of the video processor 4, the user can output a remote control signal indicating the signal format of video signals to the monitor 5, connected to the video processor 4. This enables the operation of the monitor 5 to be remotely controlled.

The CCD output signal is subjected to amplification, correlative double sampling, and the like by the analog video processing circuit 12. The processed signal is then input to an A/D conversion circuit 21, which converts the analog signal into a digital signal.

The digital signal is input to a digital former-stage video processing circuit 22, which then executes a color separating process, a matrix process, a white balance process, and the like on the signal; the color separating process separates the signal into a luminance signal and a color signal and the matrix process converts the luminance signal and color signal into an RGB signal. The resulting signals are temporarily stored in two memory blocks 23A and 23B.

The signals read from the two memory blocks 23A and 23B are subjected to signal processes for standard video signals (hereinafter referred to SDTVs or simply SDs) and for video signals (hereinafter referred to as HDTVs or simply HDs) such as high vision video signals which offer a much higher resolution than SDTVs as described below.

The signal read from the memory block 23A is input to a digital latter-stage SD processing circuit 24A, which executes a zoom-in process, an enhancing process, and the like which are compatible with SDTVs, on the signal. Subsequently, an output signal from the digital latter-stage SD processing circuit 24A is input to an SD-SDI signal generating section 25A that converts the signal into a serial video signal and to a D/A conversion circuit 26A. The SD-SDI signal generating section 25A has a serial digital interface (SDI) to convert a digital SDTV into a (digital) serial video signal. Further, the signal read from the memory block 23B is input to a digital latter-stage HD processing circuit 24B. The digital latter-stage HD processing circuit 24B executes a zoom-in process, an enhancing process, and the like which are compatible with HDTVs, on the signal.

Owing to the different aspect ratios of SDs and HDs, the digital latter-stage SD processing circuit 24A and digital latter-stage HD processing circuit 24B executes similar processes corresponding to the respective aspect ratios.

Subsequently, an output signal from the digital latter-stage HD processing circuit 24B is input to an HD-SDI signal generating section 25B that converts the signal into a serial video signal and to a D/A conversion circuit 26B.

Serial output signals from the SD-SDI signal generating section 25A and HD-SDI signal generating section 25B are input to the monitor 5 via a switch 27 through the digital video connector (digital video terminal) 31.

The switch 27 switchably selects one of the input signals in accordance with an SD/HD selection signal output by the CPU 16, for example, in response to an SD or HD selection instruction from the keyboard 17. The selected serial video signal is then input to the monitor 5 through the digital video connector 31.

Further, an analog SDTV and an analog HDTV converted by the D/A conversion circuits 26A and 26B are input to the monitor 5 via a selector 28 through the analog component video connector (analog component video terminal) 32.

Furthermore, synchronizing signals for the SDTV and HDTV, that is, SD_SYNC and HD_SYNC, from a synchronizing signal generating circuit 29 are input to the selector 28. The synchronizing signals SD_SYNC and HD_SYNC can then be input from the selector 28 to the monitor 5 via a synchronizing signal connector (synchronizing signal terminal) 33.

An input switching signal and the like from the CPU 16 are also input to the monitor 5 via a remote connector (remote terminal) 34.

Figure 2:
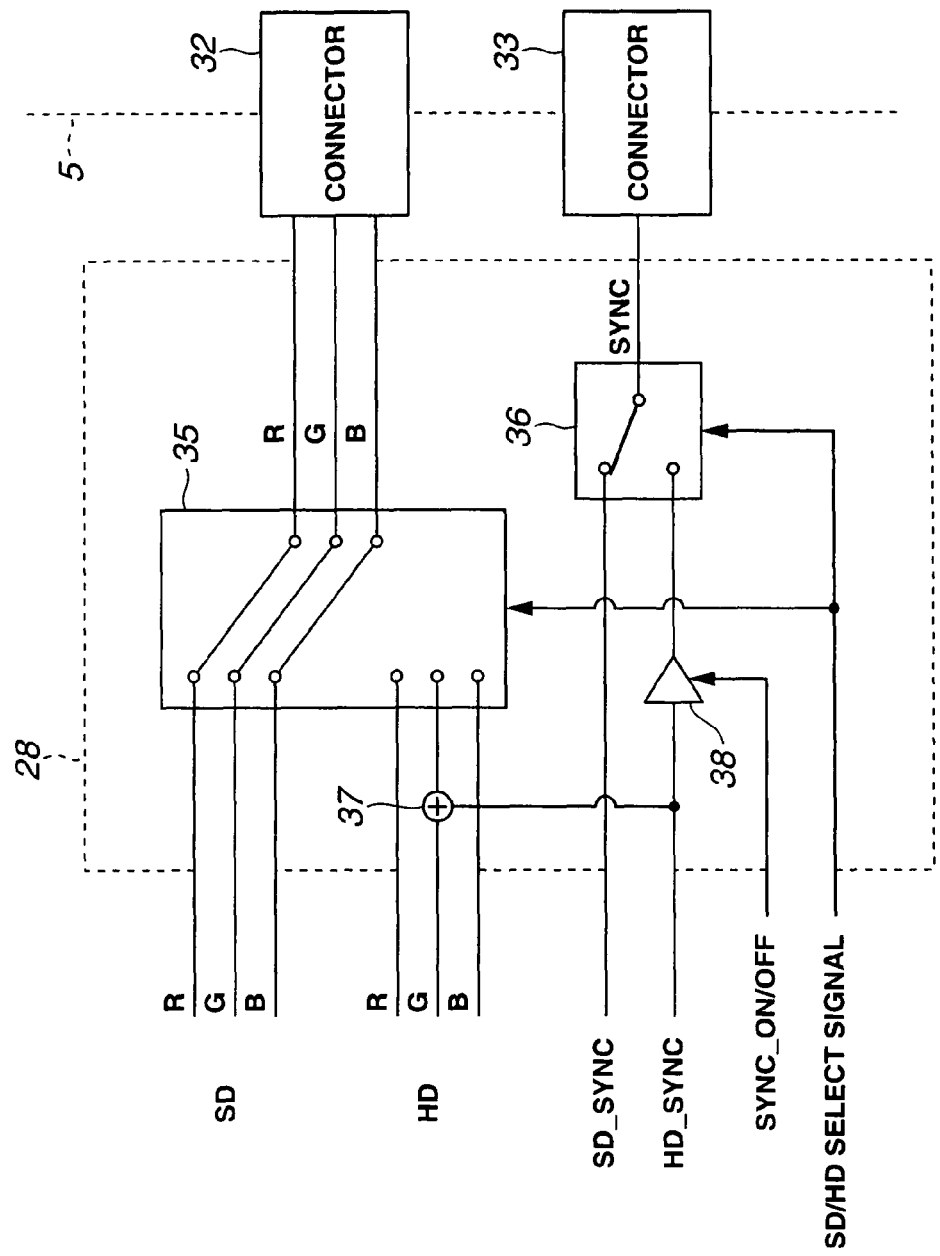
FIG. 2 is a circuit diagram showing the internal configuration of a selector.

The configuration of the selector 28 is shown in FIG. 2 in detail.

SD and HD RGB signals are input to the monitor 5 via 3-input switch 35 through the analog component video connector 32. The synchronizing signals SD_SYNC and HD_SYNC are input to the monitor 5 via a switch 36 through the synchronizing signal connector 33.

The switches 35 and 36 are switched in conjunction with each other in response to an SD/HD selection signal.

Further, the synchronizing signal HD_SYNC is added to an HD G signal by an adder 37 and input to the switch 36 via a buffer 38. Furthermore, the buffer 38 switches between an enable state in which the HD_SYNC is passed through the buffer 38 and a disable state in which the buffer 38 is deenergized, in response to a SYNC_ON/OFF signal.

That is, the synchronizing signal SD_SYNC or HD_SYNC in the video processor 4 can be input (as an external synchronizing signal) to the monitor 5 via the synchronizing signal connector 33. Instead, a video signal can be loaded from the analog component video connector 32 so that the synchronizing signal superimposed on the video signal can be synchronously separated from the video signal for use.

As shown in FIG. 1, the video processor 4 has picture-in-picture (hereinafter simply referred to as PinP) terminals T1 and T2 on its rear panel and front panel, respectively. A signal input from the terminal T1 is input to a channel CH1 of a decoder 78 via a buffer 77a. Further, a signal input from the terminal T2 is input to a channel CH2 of the decoder 78 via a buffer 77b and a detecting circuit 79 that detects signals.

Video signals input from either the terminal T1 or T2 can be adapted for PinP display before output. Further, the detecting circuit 79 makes it possible to give priority to, for example, video signals input from the terminal T2 in PinP display.

That is, a signal input from the terminal T2 causes the detecting circuit 79 to output a detecting signal to the decoder 78. In response to the detecting signal output from the terminal T2, the decoder 78 allows a signal input through the CH2 to be preferentially output to the digital latter-stage SD processing circuit 24A or digital latter-stage HD processing circuit 24B. This enables the execution of a process required for PinP display.

The decoder 78 outputs an input detecting signal to the CPU 16. In accordance with this signal, the CPU 16 sends control signals to the digital latter-stage SD processing circuit 24A or digital latter-stage HD processing circuit 24B to control it so that a PinP process is executed.

Further, as shown in FIG. 1, remote signals from the CPU 16 of the video processor 4 are input to the remote connector 34, via which the signals are sent to the monitor 5.

The remote signals include a switching signal for switching the video signal (SDTV and HDTV) input to the monitor 5 (or output by the video processor 4), an OVERSCAN_ON/OFF signal, the SYNC_ON/OFF signal, an RGB/YPbPr switching signal, and an aspect switching signal (specifically, a 5:4/4:3/16:9 switching signal).

These remote signals are input to a control circuit 41 in the monitor 5 via the remote connector 34. The control circuit 41 controls the sections in the monitor 5 in conjunction with the remote signals.

The digital serial video signal input to the digital video connector 31 is input to a selection circuit 43 via a deserializer 42 that converts a serial video signal into a parallel video signal (specifically, a YPbPr signal).

Further, an analog component video signal input from the analog component video connector 32, that is, an SDTV or HDTV RGB signal, is converted into a digital signal by the A/D converter 44. The resulting digital signal is input to the selection circuit 43. In this case, for the HDTV, the synchronizing signal superimposed on the G signal is separately extracted by a synchronous separation circuit 45 and input to a selection circuit 46.

A synchronizing signal separated from the deserializer 42 is also input to the selection circuit 46.

A digital video signal selected by the selection circuit 43 is further input to a selection circuit 47 and via a YPbPr/RGB conversion circuit 48 that converts a YPbPr signal as a Y/color difference component signal into an RGB signal. A Pb signal and a Pr signal are also called a B-Y signal and an R-Y signal, respectively.

A signal selected by the selection circuit 47 is input to an on-screen display (OSD) circuit 51 that superimposes a graphic image such as a menu on a screen of a display panel 53 for display, via a zoom-in and zoom-out circuit 49 that performs a zoom-in operation and a zoom-out operation.

The control circuit 41 controls turn-on and -off of screen display by the OSD circuit 51, selections by the selection circuits 43, 46, 47, and zoom-in and zoom-out operations by the zoom-in and zoom-out circuit 49.

An output signal from the OSD circuit 51 is input to the display panel 53, composed of a liquid crystal display or the like, via a display control circuit 52 that executes a display control process. The display panel 53 displays endoscopic images and the like captured by the CCD 9I.

Further, a synchronizing signal selected by the selection circuit 46 is input to a format identification circuit 54 that determines either the SDTV or HDTV format and to a timing control circuit 55 that controls timings.

The format identification circuit 54 sends information on the identified format, either the SDTV or HDTV, to the control circuit 41 and timing control circuit 55. The control circuit 41 performs control corresponding to the identified format.

Further, the timing control circuit 55 sends a timing signal corresponding to the identified format to the display control circuit 52, which executes a display control process corresponding to the identified format.

Overscan in accordance with the present embodiment will be supplementarily described with reference to FIG. 3.

Figure 3:
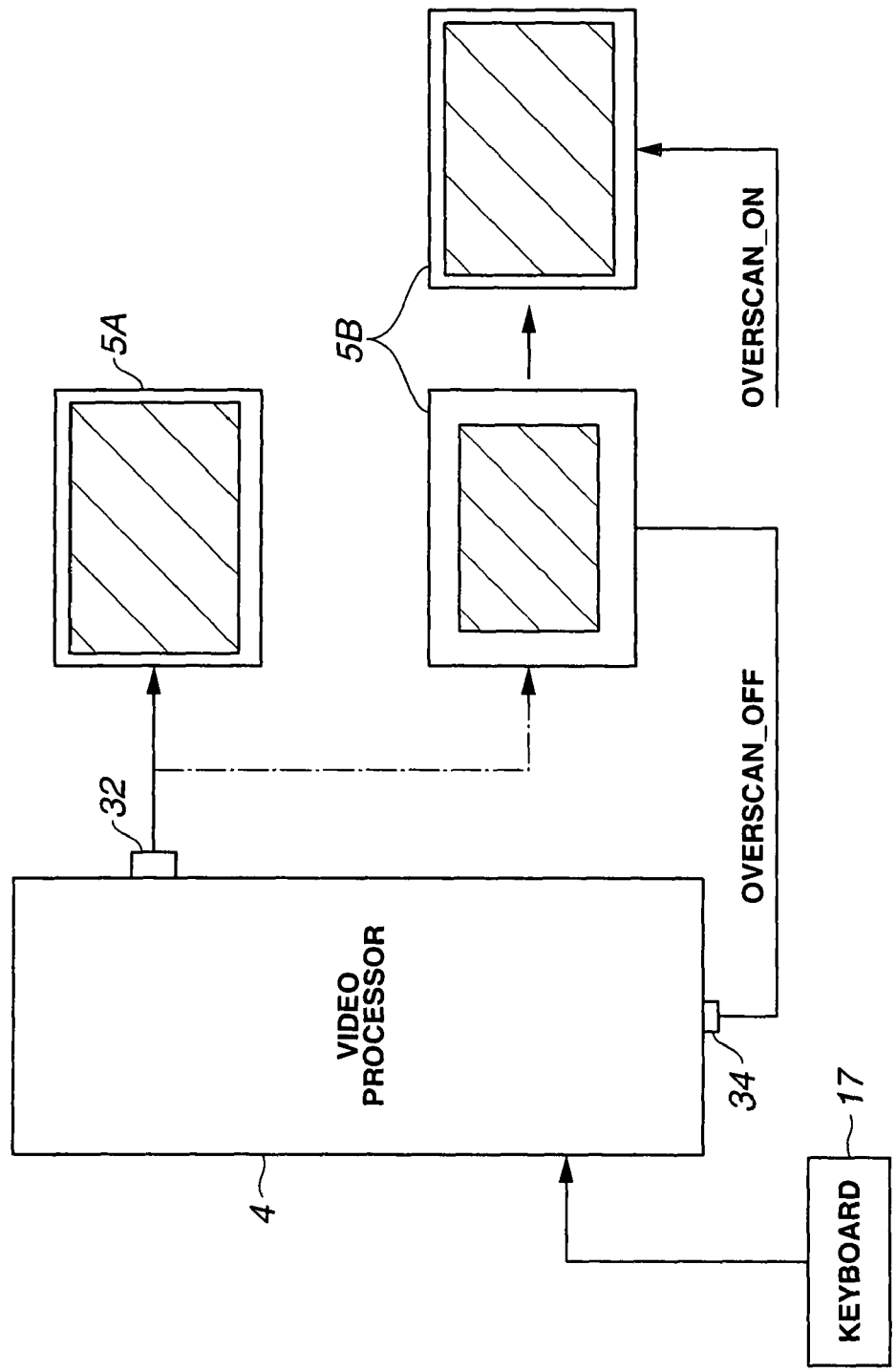
FIG. 3 is a diagram illustrating the operation of an overscan mode.

As described above, the present embodiment provides an overscan mode and can use either a CRT monitor 5A or an LCD monitor 5B as the monitor 5 as shown in FIG. 3. In FIG. 1, the monitor 5 represents the CRT monitor 5A and LCD monitor 5B. In the monitor 5 in FIG. 1, the use of an LCD display (LCD panel) as the display panel 53 corresponds to the LCD monitor 5B.

In FIG. 3, an SDTV displayed on the LCD monitor 5B appears smaller than the same SDTV displayed on the CRT monitor 5A (case where the overscan mode is off as shown in FIG. 3). Thus, to display an SDTV on the LCD monitor 5B, the overscan mode is turned on to allow the SDTV to appear almost as large as the same SDTV displayed on the CRT monitor 5A (case where the overscan mode is on as shown in FIG. 3). This control can be performed by the OVERSCAN_ON/OFF signal contained in a monitor remote signal.

The LCD monitor 5B in this case can be overscanned. The video processor 4 outputs not only SDTV video signals but also an overscan monitor remote signal to the LCD monitor 5B.

In particular, an attempt to display a 4:3 SD image on the LCD monitor 5B in an aspect ratio of 5:4 may cause the image to appear smaller.

Accordingly, under these conditions, the video processor 4 outputs the overscan monitor remote signal to the LCD monitor 5B to allow the image to appear larger on the display panel of the LCD monitor 5B.

Thus, in the case of using the LCD monitor 5B as the monitor 5, when at least SDTVs are output from the video processor 4 and to display a 4:3 SD image in an aspect ratio of 5:4, by turning on the overscan mode, the image can appear as large as the same image displayed on the CRT monitor 5A.

Now, the PinP function in accordance with the present embodiment will be supplementarily described with reference to FIGS. 4A and 4B.

As described above, the video processor 4 in accordance with the present embodiment comprises the function for PinP display. That is, the video processor 4 can reduce an external input image as an external input when superimposing it on an endoscopic image input by the scope 2I.

Figure 4A:
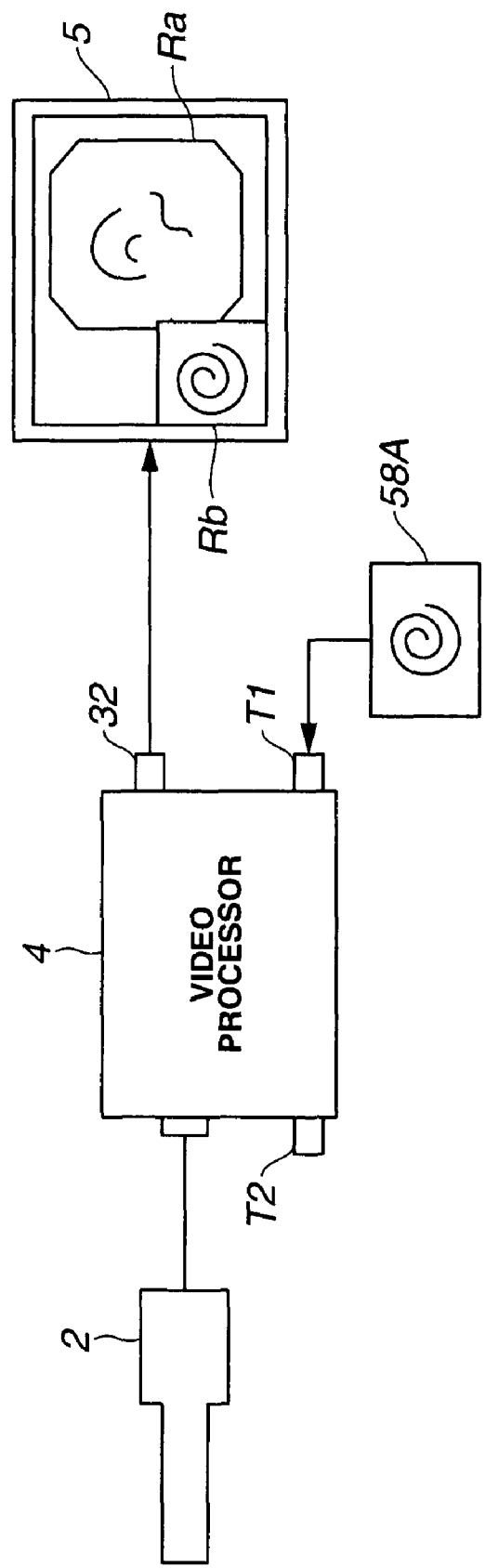
FIG. 4A is a diagram illustrating a PinP display function provided when a signal is input to one external input terminal.
Figure 4B:
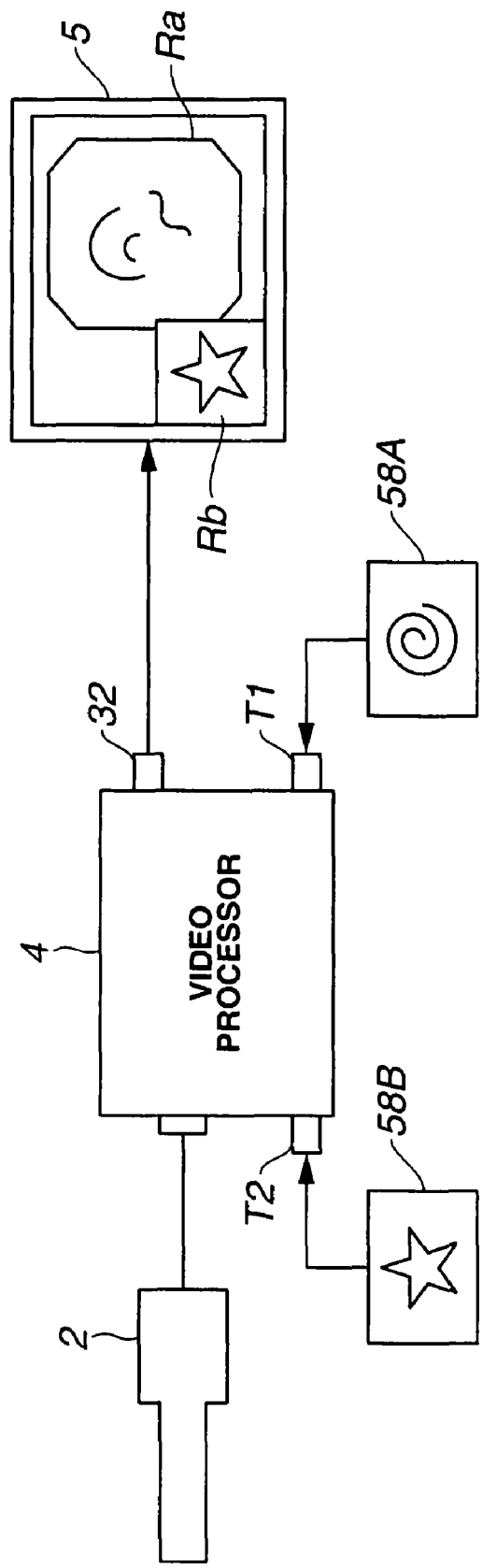
FIG. 4B is a diagram illustrating a PinP display function provided when signals are input to both external input terminals.

In this case, as shown in FIGS. 4A and 4B, the video processor 4 comprises the external input terminals T1, T2 for PinP input.

One of the external input terminals T1, T2 (specifically, T2) is provided on the same surface as an operation panel of the video processor 4. The other terminal T1 is provided on a rear surface or a side surface of the video processor 4.

For example, as shown in FIG. 4A, an input signal input by an external image output device 58A is displayed on the display surface of the monitor; the external image output device 58A is connected to one of the two external input terminals T1 and T2. Specifically, an endoscopic image is displayed in an endoscopic image display area Ra in the display surface of the monitor 5, while the external image input by the external image output device 58A is displayed smaller in a PinP display area Rb as a child screen; the PinP display area Rb is located in the lower right of the screen adjacent to the endoscopic image display area Ra.

Further, if two external image output devices 58A, 58B input input signals to the respective input terminals T1, T2 as shown in FIG. 4B, the external image input to the input terminal T2 on the operation panel, which is easily removable, is preferentially subjected to PinP display.

Figure 5:
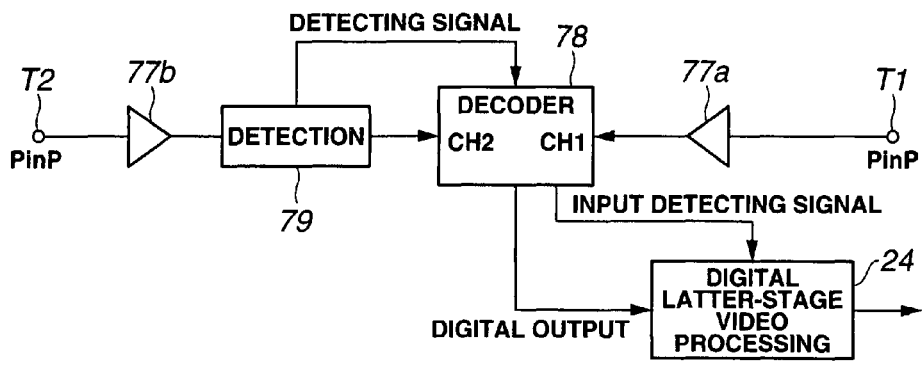
FIG. 5 is a block diagram showing the configuration of a PinP processing section.

FIG. 5 shows the configuration of periphery of a PinP signal processing section. As shown in FIG. 1, the video processor 4 has the PinP terminals T1 and T2 on the rear surface (rear panel) and operation panel (front panel), respectively.

A signal input from the terminal T1 is input to the channel CH1 of the decoder 78 via the buffer 77a. Further, a signal input to the terminal T2 is input to the channel CH2 of the decoder 78 via the buffer 77b and the detecting circuit 79 that detects signals.

Without any signal input from the front side, an input signal from the rear side is converted into a digital output signal from the decoder 78, which is sent to the digital latter-stage video processing circuit 24 (FIG. 5 collectively shows the digital latter-stage SD video processing circuit 24A and digital latter-stage HD video processing circuit 24B in FIG. 1).

An input signal from the front side causes the detecting circuit 79 to generate an input detecting signal, which is sent to the decoder 78 to select the channel CH2.

In FIG. 5, an input signal input from the terminal T1 or T2 causes the decoder 78 to input the input detecting signal to the digital latter-stage video processing circuit 24. If two signals are input to the respective terminals, the decoder 78 gives priority to the one from the terminal T2.

Thus, the present embodiment provides the two types of PinP inputs, the front input and rear panel input, and gives priority to the front input. In FIG. 5, the input detecting signal is input directly to the digital latter-stage video processing circuit 24. However, similar control may be performed via the CPU 16 as shown in FIG. 1.

In the present embodiment configured as described above, the video processor 4 comprises the function for executing the signal processes for the scope 2A, containing the CCD 9 for SDTVs, and the scope 2, containing the CCD 9 for HDTVs.

The video processor 4 can output SDTV and HDTV video signals, offering different resolutions, to the monitor 5 via the common connector; the monitor serves as an external video display instrument. The user can (instructively) select an output video signal and the display format (aspect ratio) via the keyboard 17.

Further, the selection information can be sent, by the CPU 16, to the control circuit 41 in the monitor 5 via the remote connector 34. The control circuit 41 in the monitor 5 can execute a signal process corresponding to the selection to display the (instructively) selected video signal in the selected aspect ratio.

For example, either SDTV video signals or HDTV video signals can be selectively output via the keyboard 17, and both SDTVs and HDTVs can be output either as analog component video signals or as digital serial video signals.

It is also possible to select the output of a synchronizing signal superimposed on a video signal or the output, from the synchronizing signal connector 33, of a synchronizing signal generated by the video processor 4. Description will be given of operations in the present embodiment configured as described above.

If the scope 2I is connected to the video processor 4 as shown in FIG. 1, its scope ID code of the scope 2I is detected by the scope ID detecting circuit 14 in the video processor 4 and sent to the CPU 16 via detecting information. On the basis of the detecting information, the CPU 16 controls the CCD driver 11 to drive the CCD 9I, mounted in the scope 2I. An output signal from the CCD 91 is converted into a digital signal by the A/D conversion circuit 21 via the analog video processing circuit 12. The digital signal is then subjected to color separation, a matrix process, and the like by the digital former-stage video processing circuit 22 and thus converted into an RGB signal. The RGB signal is then written to the memory block 23A or 23B.

In this case, for the CCD 9A for SDTVs, the RGB signal is written to the memory block 23A. For the CCD 9B for HDTVs, the RGB signal is written to the memory block 23B.

The digital SDTV RGB signal written to the memory block 23A is read and subjected to a zoom-in process, an enhancing process, and the like by the digital latter-stage SD processing circuit 24A. The SDTV RGB signal is then converted into a serial video signal, which is input to the switch 27. The digital HDTV RGB signal written to the memory block 23B is read and subjected to a zoom-in process, an enhancing process, and the like by the digital latter-stage HD processing circuit 24B. The HDTV RGB signal is then converted into a serial video signal, which is input to the switch 27.

The digital serial SDTV or HDTV input to the switch 27 is output to the monitor 5 through the digital video connector 31.

The digital SDTV or HDTV RGB signal from the digital latter-stage SD processing circuit 24A and digital latter-stage SD processing circuit 24B is converted into an analog signal by the D/A conversion circuit 26A, 26B. The analog signal is output to the monitor 5 via the selector 28 through the analog component video connector 32.

The synchronizing signals SD_SYNC, HD_SYNC generated in the video processor 4 can also be output to the monitor 5 through the synchronizing signal connector 33.

When the user selects and indicates a signal to be output to the monitor 5, to the CPU 16 via the keyboard 17, the selected and indicated video signal is output to the monitor 5.

Further, information corresponding to the selective indication is sent to the control circuit 41 in the monitor 5 through the remote connector 34 as a remote signal.

As described above, by performing a (instructive) selecting operation via the keyboard 17, the user can select the video signal to be output from the video processor 4 to the monitor 5, the aspect ratio, and the like. Further, after selecting either the SDTV or HDTV video signal, the user can also select an output in component video signal (RGB signal) format, an output in digital serial video signal (SDI) format, or an output in digital Y/color difference component signal (YPbPr signal) format.

In accordance with these selections, the selection information is sent to the control circuit 41 in the monitor 5. The control circuit 41 controls the display signal processing system in the monitor 5 in accordance with the selections.

For example, selection of an HDTV digital Y/color difference component signal (YPbPr signal) allows the monitor 5 to convert the digital serial video signal input from the digital video connector 31 into a YPbPr signal as a parallel digital Y/color difference component signal via the deserializer 42.

In this case, in the control circuit 41, in accordance with the information transmitted through the remote connector 34, the selection circuit 43 controllably passes the signal from the deserializer 42. Further, the selection circuit 47 controllably passes the signal from the selection circuit 43. Consequently, an image is displayed on the display panel 53 of the monitor 5 on the basis of the HDTV YPbPr signal. Further, in this case, the aspect ratio can be selected so that the image can be displayed on the display panel 53 in the selected aspect ratio.

With a digital RGB signal selected instead of the HDTV digital Y/color difference component signal (YPbPr signal), the control circuit 41 switchably controls so that the selection circuit 47 passes an output signal from the YPbPr/RGB conversion circuit 48.

In the above case, selection of an analog RGB signal instead of the digital one allows the analog RGB signal output from the analog component video connector 32 to be converted into a digital RGB signal by the A/D conversion circuit 44. The digital RGB signal passes through the selection circuit 43 which has selections controlled by the control circuit 41, and then through the selection circuit 47. The resulting signal is output to the display panel 53.

With an SDTV selected instead of the HDTV, an operation corresponding to the selection of the SDTV is performed.

Further, it is also possible to select either the synchronous separation, from a video signal, of a synchronizing signal input to the monitor 5 or external synchronization, not internal synchronization based on synchronous separation.

For example, with the HDTV digital Y/color difference component signal (YPbPr signal) selected and further the internal synchronization selected, the control circuit 41 allows a synchronizing signal from the deserializer 42 to be input to the timing control circuit 55 via the selection circuit 46.

In this case, selection of the external synchronization causes the control circuit 41 to controllably input the synchronizing signal HD_SYNC from the synchronizing signal connector 33 to be input to the timing control circuit 55 via the selection circuit 46.

Further, with the HDTV analog RGB signal selected and further the internal synchronization selected, the synchronizing signal is separated, by the synchronous separation circuit 45, from the RGB signal input to the monitor 5 through the analog component video connector 32. The RGB is input to the timing control circuit 55 via the selection circuit 46 selected and controlled by the control circuit 41. An almost similar operation is performed for the synchronizing signal for the SDTV.

Thus, the present embodiment enables plural types of video signals offering different resolutions to be output from the common video connectors 31, 32. This simplifies connection operations to improve the operability for endoscopic examinations. The occupied space can also be reduced, enabling a reduction in the size of the video processor 4.

Further, information on a video signal output by the video processor 4 is sent to the control means in the monitor 5, which controls the internal signal processing system of the monitor 5 in accordance with the information. This eliminates switching operations, allowing operability to be improved.

In the above description, as shown in FIG. 2, an RGB video signal is output from the analog component video connector 32 via the selector 28. However, instead of the RGB signal, a luminance/color difference component signal, that is, a YPbPr signal, may be output from an analog luminance/color difference component video connector.

In this case, the synchronizing signal superimposed on an HDTV luminance signal Y is separated by the synchronous separation circuit 45.

Now, a variation of PinP display will be described with reference to FIG. 6. In the present variation, if the scope 2I connected to the video processor 4 is the HDTV-compatible scope 2B, HDTV signals are output to the monitor 5. However, an input signal for PinP display, for example, an SDTV format from an ultrasonic diagnosis apparatus through an external terminal needs to be subjected to a signal process such that the HDTV and SDTV are synthesized.

The present variation deals with this case. The present variation also deals with a synthesizing method for the case where the scope 2A connected to the video processor 4 is for SDTVs (more specifically, the CCD 9I mounted in the scope 2A is for SDTVs).

Figure 6:
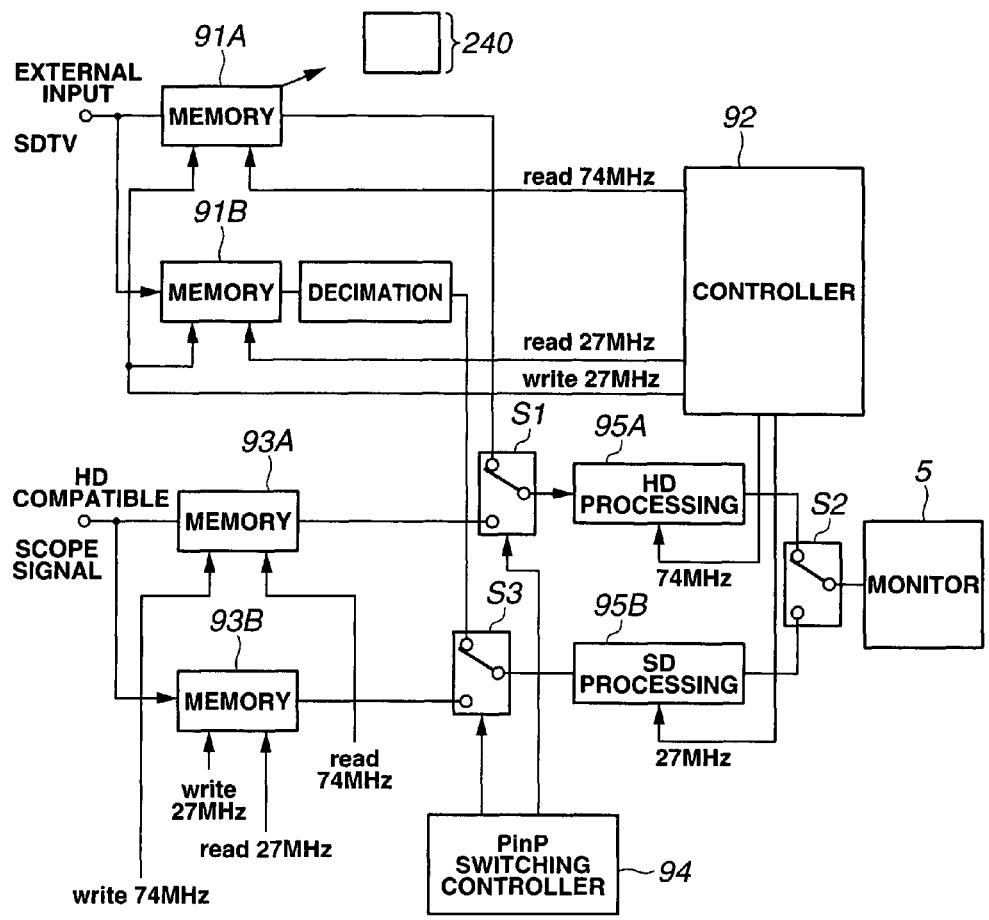
FIG. 6 is a diagram showing the configuration of a variation of the PinP processing section.

First, the operation in FIG. 6 will be generally described. With the HDTV-compatible scope 2B connected, an external SDTV video signal is temporarily stored (written to) in the memory and read at 74 MHz as is the case with reading from the HDTV memory. Further, the external input and the scope image are switched at a PinP timing to superimpose PinP on the image. The resulting image is subjected to an HD process, and the processed signal is output to the monitor 5.

On the other hand, with the SDTV-compatible scope 2A connected, an external SDTV video signal is stored in the memory and read at 27 MHz. The video signal is then decimated both in a horizontal direction and in a vertical direction. The decimated external SDTV video signal and the scope image are switched at a PinP timing for PinP display. Thus, the method for PinP synthesis is switched depending on the actually connected scope 2I. This will be specifically described below with reference to FIG. 6.

As shown in FIG. 6, (after being converted into a digital signal by an A/D converter (not shown)) an external SDTV video signal input from the external input terminal is written to field memories 91A, 91B under the control of a controller 92 in accordance with a 27-MHz clock.

Further, a signal read from the CCD 9B of the HD-compatible scope 2B is subjected to an analog process and an A/D conversion process and then written to a field memory 93A under the control of the controller 92 in accordance with a 74-MHz clock.

As shown in the figure, the field memory 91A (and 91B) has 240 pixel lines in a vertical direction. The field memory 91A is used for PinP display for HDTVs, whereas the field memory 91B is used for PinP display for SDTVs. On the other hand, the field memory 93A has 480 pixel lines in the vertical direction.

Further, read operations are performed on the field memories 93A and 91A in accordance with the 74-MHz clock. Signals read from the field memories 91A and 93A are input to an HD processing circuit 95A via a switch S1 that performs high-speed switching operations under the control of a PinP controller 94. That is, either a scope signal or an external SDTV video signal is selected at a PinP display frame corresponding to a boundary. Both signals are superimposed on each other and the resulting signal is input to the HD processing circuit 95A.

The 74-MHz clock from the controller 92 is input to the HD processing circuit 95A, which executes a signal process corresponding to an HD format in synchronism with the clock. The output signal from the HD processing circuit 95A is output to the monitor 5 via a selection switch S2. In accordance with an instruction input from the keyboard 17 or the like, the selection switch S2 performs a switching operation to turn on the HD processing circuit 95 via the CPU (not shown).

Figure 7A:
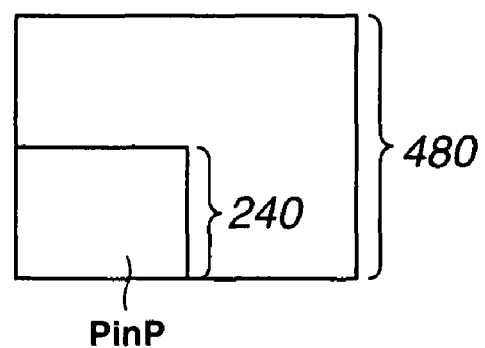
FIG. 7A is a diagram illustrating PinP in an HD field image in FIG. 6.

In this case, as in an HD field image shown in FIG. 7A, an image based on an external SDTV video signal is PinP-displayed in an image from the CCD 9B of the HD compatible scope 2B; the former comprises 240 pixel lines and the latter comprises 480 pixel lines in the vertical direction.

Figure 7B:
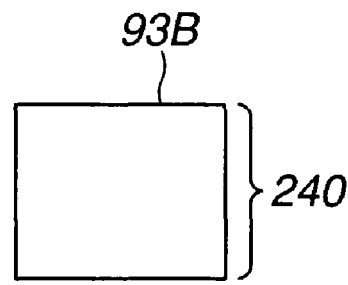
FIG. 7B is a diagram showing the size of a field memory in FIG. 6.

On the other hand, with the SD compatible scope 2A, a signal read from the CCD 9A of the scope 2A is subjected to an analog process and an A/D conversion process. The processed signal is written to the field memory 93B in accordance with the 27-MHz clock under the control of the controller 92. As shown in FIG. 7B, the field memory 93B has 240 pixel lines in the vertical direction.

Read operations are performed on the field memories 93B and 91B in accordance with the 27-MHz clock. A signal read from the field memory 93B is input to an SD processing circuit 95B via a switch S3 that performs high-speed switching operations under the control of the PinP controller 94.

On the other hand, a signal read from the field memory 91B is decimated both in the horizontal direction and in the vertical direction by a decimation circuit 96. The resulting signal is input to the SD processing circuit 95B via the switch S3. The 27-MHz clock from the controller 92 is input to the SD processing circuit 95B, which executes a signal process corresponding to an SD format in synchronism with the clock. The output signal from the SD processing unit 95B is output to the monitor 5 via a selection switch S2.

Figure 7C:
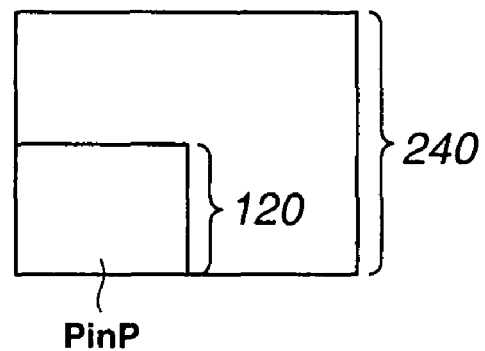
FIG. 7C is a diagram illustrating PinP in the SD field image in FIG. 6.

For an SD field image in this case, as shown in FIG. 7C, an image based on an external SDTV video signal is PinP-displayed in an image from the CCD 9A of the SD compatible scope 2A; the former comprises 120 pixel lines and the latter comprises 240 pixel lines in the vertical direction.

According to the present variation, the HD compatible scope 2B enables even externally input external SDTVs to be PinP-displayed in spite of its simple configuration. The SD compatible scope 2A also enables input external SDTVs to be PinP-displayed in spite of its simple configuration.

Now, with reference to FIG. 8A, description will be given of configuration of a noise reduction filter peripheral section provided in the digital former-stage video processing circuit 22 in FIG. 1.

Figure 8A:
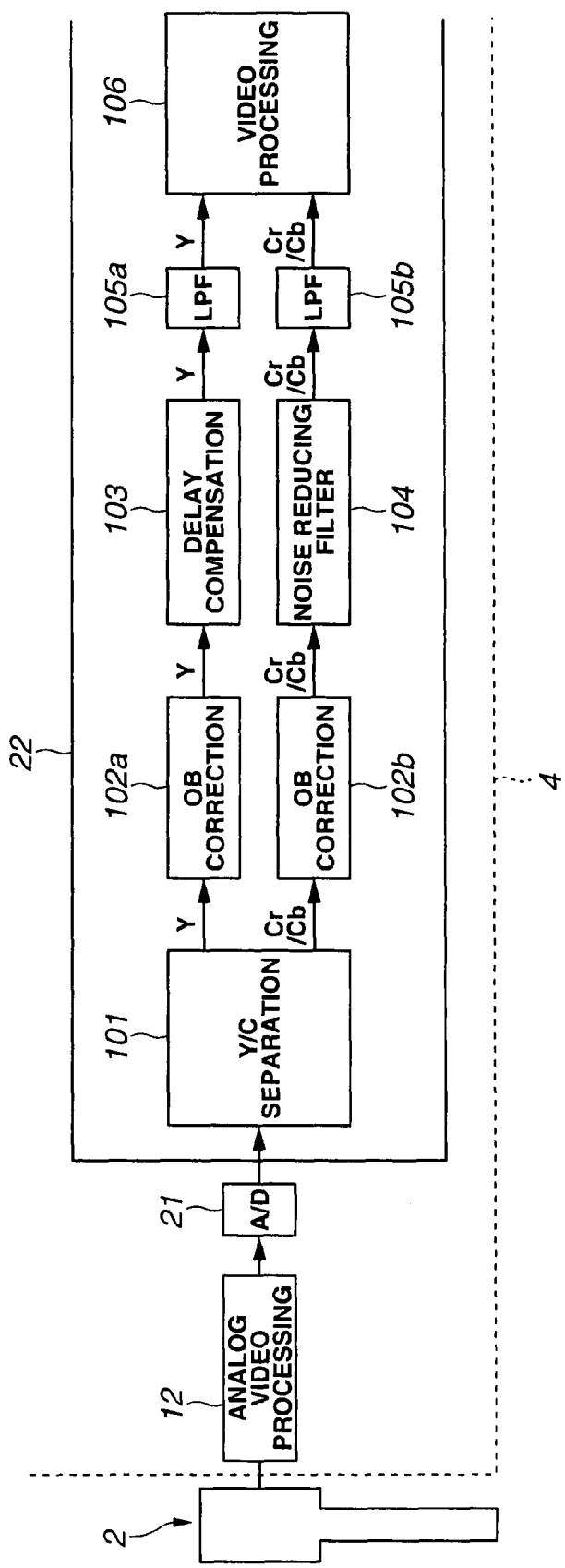
FIG. 8A is a diagram illustrating an example of configuration of a digital former-stage video processing circuit and a noise reduction filter process.

As shown in FIG. 8A, a digital video signal from the A/D conversion circuit 21 is input to a Y/C separation circuit 101 in the former-stage video processing circuit 22. The signal is then separated into a luminance signal Y and a color signal Cr/Cb (or C), which are input OB correction circuits 102a, 102b, respectively.

The luminance signal Y and color signal Cr/Cb are subjected to optical black correction process (OB correction) by the OB correction circuit 102a, 102b. The processed signals are input to a delay compensation circuit 103 and a noise reduction filter 104, respectively. The delay compensation circuit 103 compensates for a delay in the luminance signal Y (which corresponds to a delay in the noise reduction filter process with respect to the color signal Cr/Cb). The delay-compensated luminance signal is input to a succeeding LPF 105a, where the signal is subjected to a low pass filter process.

Figures 8B, 9A:
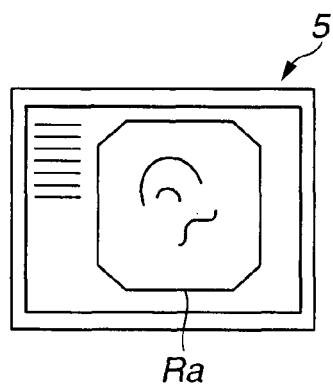
FIG. 8B is a diagram illustrating a noise reducing process executed by the noise reduction filter.
FIG. 9A is a diagram showing an example of a normal image display.

Further, the noise reduction filter 104 executes a noise reduction process of generating a color signal value S25 for a shaded pixel P25 in the center of 9×3 pixels P11 to P39 from color signals Cr/Cb (denoted by S11 to S39) for the pixels as shown in FIG. 8B.

Specifically, the noise reduction filter 104 generates S=(S11+S12+ . . . +S39)/27.

Each color signal Cr/Cb output by the noise reduction filter 104 is subjected to a low pass filter by the LPF 105b. The processed signal is input to a video processing circuit 106 together with the luminance signal Y. These signals are then subjected to another process.

Thus, the digital former-stage video processing circuit 22 executes a noise reduction filter process only on a color signal C resulting from a Y/C separation. The digital former-stage video processing circuit 22 is followed by an LPF. For the above PinP, a display method such as shown below may be implemented.

Figure 9B:
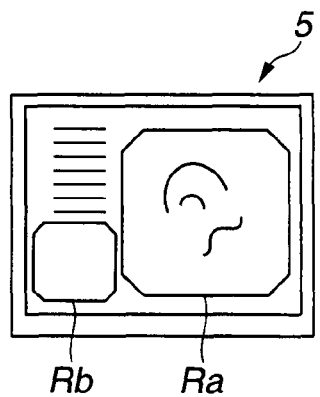
FIG. 9B is a diagram showing an example of a PinP image display.

FIG. 9A shows a display state for normal observation showing no PinP image. In this display state, an endoscopic image display area Ra appears at a position closer to the center than the right end of the screen. In contrast, in PinP display, a PinP image is displayed so as not to overlap the endoscopic image in the endoscopic image display area Ra with the endoscopic image display area Ra shifted toward a side opposite to a PinP display area Rb as shown in FIG. 9B. In this case, the endoscopic image display area Ra is shifted rightward.

Figure 9C:
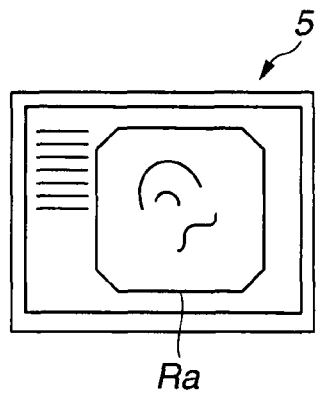
FIG. 9C is a diagram showing an example of an image display in the normal image display state obtained by canceling the PinP state in FIG. 9B.

Further, if the PinP image is lost, the loss is determined on the basis of the input detecting signal to switch to a full screen mode as shown in FIG. 9C. In this case, the endoscopic image display area Ra is shift to a display position similar to that shown in FIG. 9A.

Furthermore, the absence of a PinP image (as determined on the input detecting signal) disables the selection of a PinP image. This prevents a switching operation from being achieved even by depressing a scope switch (not shown) provided on the scope 2.

Figure 10A:
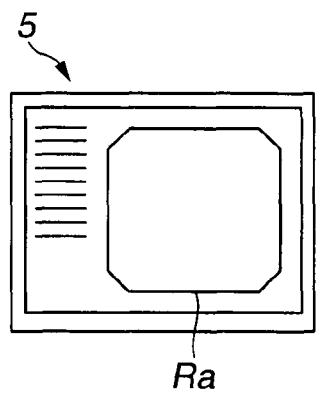
FIG. 10A is a diagram showing an example of display of an endoscopic image for normal observation.
Figure 10B:
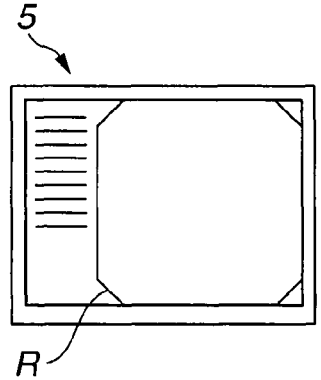
FIG. 10B is a diagram showing an example of display in which the endoscopic image is zoomed in across a display screen as a result of operation of a zoom-in switch.
Figure 10C:
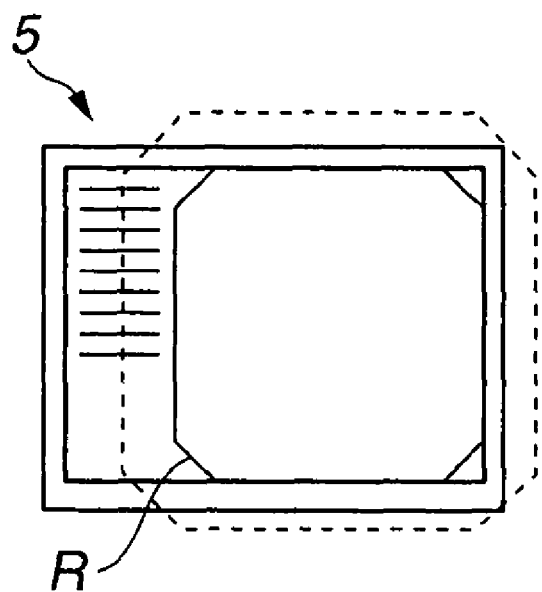
FIG. 10C is a diagram showing an example of display in which the zoom-in switch is further operated in the state in FIG. 10B.

Images may be zoomed in as shown in FIGS. 10A to 10C. FIG. 10A shows an example of display of an endoscopic image for normal observation.

In this case, an endoscopic image is displayed in the predetermined endoscopic display area Ra set in the display screen of the monitor 5. In this state, operation of the zoom-in switch performs an electronic zoom-in operation until the endoscopic image is displayed across the screen in the vertical direction as shown in FIG. 10B. That is, the image is zoomed in up to a display frame R for a full screen in the vertical direction.

A further operation of the zoom-in switch allows the full-screen display frame R state to be maintained with the inside of the zoomed-in endoscopic image displayed in the display frame R as shown in FIG. 10C. That is, the zoom-in instruction causes the zoomed-in state in FIG. 10B to be further zoomed in. However, the size of the zoomed-in endoscopic image is larger than the full screen (as shown by a dotted line in FIG. 10C). Accordingly, only the part of the image which is contained in the full screen is displayed.

Figure 11:
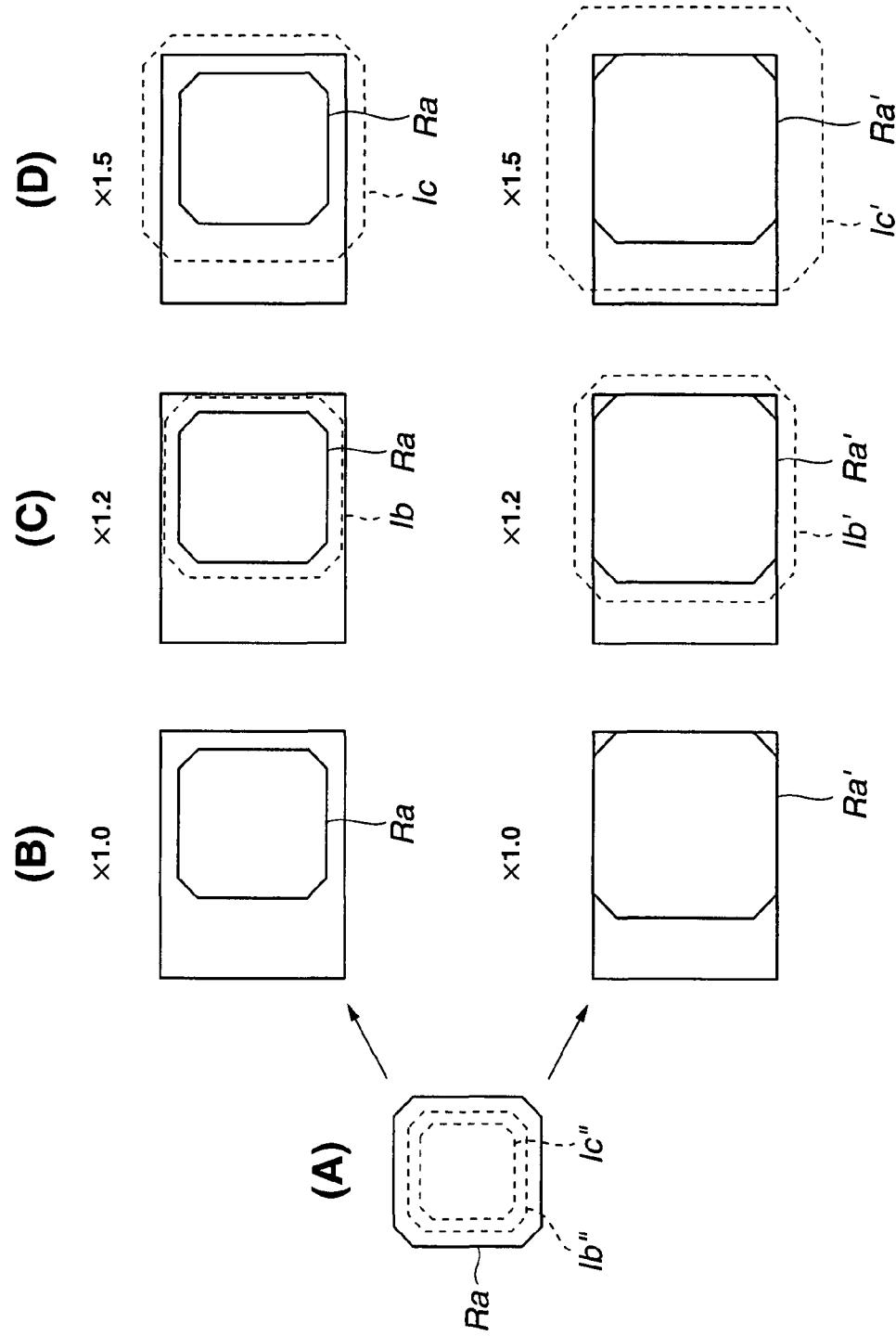

Now, with reference to FIG. 11, description will be given of a method for zooming in an image in accordance with a variation. The present variation executes an electronic zooming process of using the endoscopic image display area Ra as a display frame and providing, for example, a 1.0-, 1.2-, or 1.5-times zoom-in display in the area Ra in response to operation of the zoom-in switch. A solid line in FIG. 11A shows the size of a normally displayed endoscopic image in the endoscopic image display area Ra.

Accordingly, a normal (that is, the scale is 1.0) monitor display screen is displayed as shown in the upper and lower parts of FIG. 11B depending on the sizes of endoscopic image display areas Ra, Ra'. Then, when the zoom-in switch is operated to output a 1.2-times zoom-in instruction signal, a zoom-in circuit (zoom-in/zoom-out circuit shown in FIG. 12) executes an electronic zooming process to zoom in the image up to 1.2 times as shown in the upper and lower parts of FIG. 11C.

In FIG. 11C, dotted lines Ib, Ib' show sizes of the entire endoscopic image in FIG. 11B zoomed in up to 1.2 times. Actually, only the part of the image which is contained in the endoscopic image display area Ra is zoomed in to be displayed. In FIG. 11A, the zoomed-in display corresponds to the part shown by a dotted line Ib".

When the zoom-in switch is further operated to output a 1.5-times zoom-in instruction signal, a zoom-in process is executed to zoom in the image up to 1.5 times as shown in the upper and lower parts of FIG. 11D.

In FIG. 11D, dotted lines Ic, Ic'show the sizes of the entire endoscopic image in FIG. 11B zoomed in up to 1.2 times. Actually, only the part of the image which is contained in the endoscopic image display area Ra is zoomed in to be displayed. In FIG. 11A, the zoomed-in display corresponds to the part shown by a dotted line Ic".

Now, description will be given of configuration of the zoom-in/zoom-out circuit that executes such an electronic zoom-in process (having a function for executing a zoom-out process) as described above.

Figure 12:
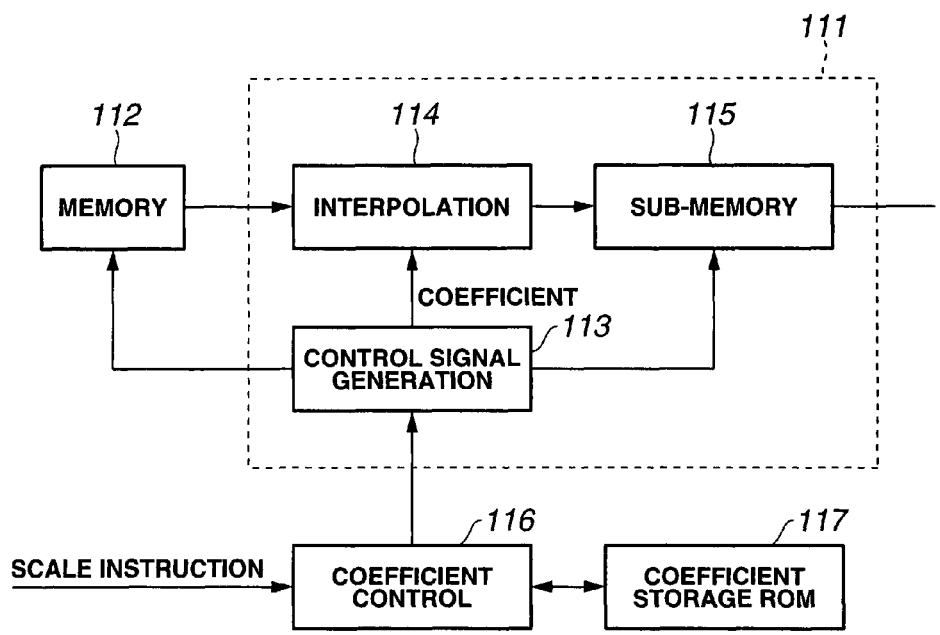
FIG. 12 is a block diagram showing an example of configuration of a zoom-in circuit.
Figure 13:
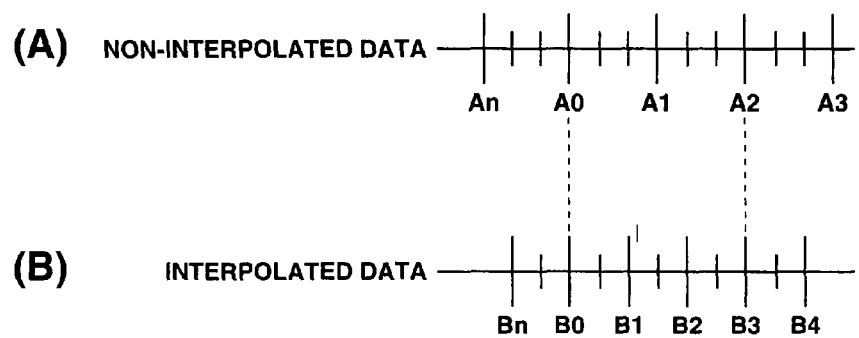
FIG. 13 is a diagram illustrating the operation of a 1.5-times zoom-in operation.

FIG. 12 shows the configuration of a zoom-in/zoom-out circuit 111 provided in, for example, the digital latter-stage SD processing circuit 24A to execute electronic zoom-in and zoom-out operations. The example described below relates to luminance signals (similar arrangements and processes are used for color signals).

Signal data is stored in the memory 112 (in the example in FIG. 1, a luminance signal storage memory in the memory block 23A). Pixel data corresponding to a read signal (addresses) from a control signal generating circuit 113 is read from the memory 112 and input to an interpolation circuit 114.

The interpolation circuit 114 interpolates the pixel data input by the memory 112 by multiplying the pixel data by a coefficient output by the control signal generating circuit 113. The interpolation circuit 114 stores the interpolated pixel data in a sub-memory 115.

Further, a zoom-in/zoom-out scale instruction from the external keyboard 17, the zoom-in switch, or the like is input to a coefficient control circuit 116. The coefficient control circuit 116 reads coefficient information corresponding to the scale for the zoom-in instruction, from a coefficient storage ROM 117 that stores coefficient information corresponding to scale instructions. The coefficient control circuit 116 then sends the read information to the control signal generating circuit 113.

FIGS. 13A and 13B show uninterpolated data and interpolated data for a 3/2 (1.5) times zoom-in process, for example.

Adjacent data are defined as A, B, interpolation data to be determined is defined as C, and zoom-in/zoom-out coefficients are defined as $\alpha$, $\alpha 2$. Then, $C=\alpha A+\alpha 2B$. Since $\alpha+\alpha 2=1$, this equation can be transformed into $C=B+\alpha(A-B)$.

A zoom-in operation will be described with reference to FIGS. 13A and 13B.

For a 3/2 times zoom-in operation, the adjacent images are interpolated to generate information on three pixels shown at B0-B1, B1-B2, B2-B3 from a video signal for two pixels shown at A0-A1, A1-A2. The adjacent images are weighted on the basis of the distance between an origin position (A0-A2) and the video signal, the original image, to generate interpolated data as follows.

$B0\text{-}B1(\text{origin position } B0) = 0/3 * An + 3/3 * A0 (= A0)$ $B1\text{-}B2(\text{origin position } B1) = 1/3 * A0 + 2/3 * A1$ $B2\text{-}B3(\text{origin position } B2) = 2/3 * A1 + 1/3 * A2$ $B3\text{-}B4(\text{origin position } B3) = 3/3 * A2 + 0/3 * A3 (= A2)$ The interpolated data is stored in the sub-memory 115. Reading the stored data from the sub-memory 115 allows the 3/2-times zoomed-in data to be output to the succeeding component.

Figure 14A:
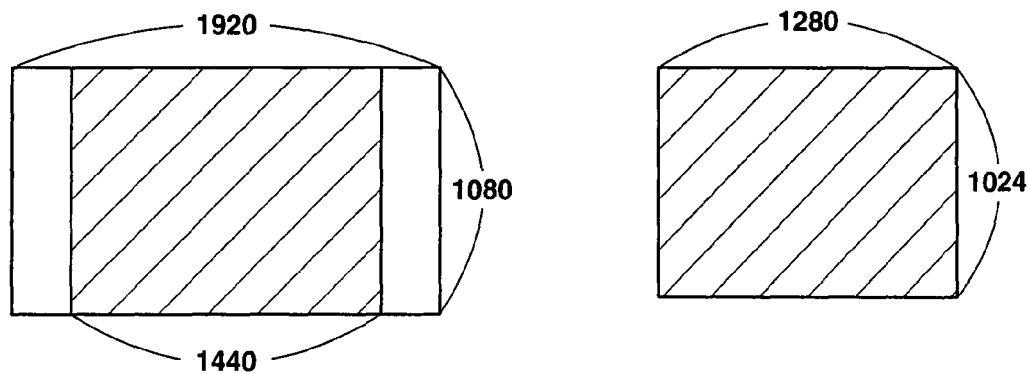
FIG. 14A is a diagram illustrating an operation of displaying an HDTV image on a liquid crystal monitor in an aspect ratio of 4:3.
Figure 14B:
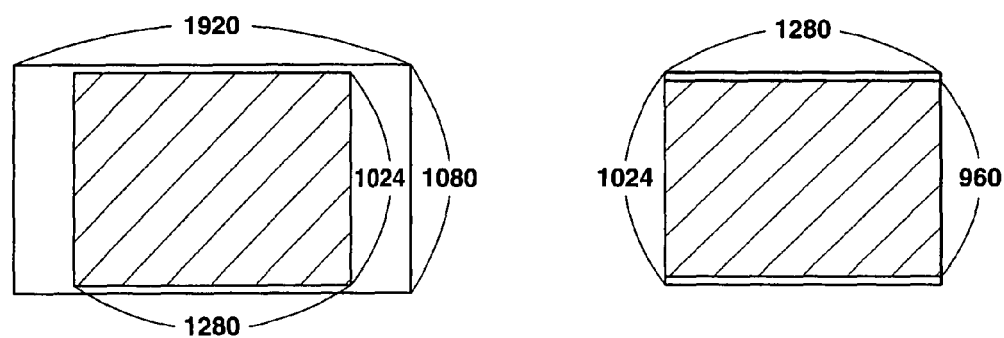
FIG. 14B is a diagram illustrating an operation of displaying an HDTV image on a liquid crystal monitor at an aspect ratio of 5:3.

Now, with reference to FIGS. 14A and 14B, description will be given in respect of the HDTV format and the LCD monitor 5B and that the video processor 4 sets a zoom-in scale in association with a display setting (aspect ratio setting) of the LCD monitor 5B. In FIGS. 14A and 14B, the left diagram shows the image size of the HDTV format, whereas the right diagram shows the display size of the LCD monitor 5B.

As shown in FIG. 14A, the HDTV format comprises 1920 pixels in the horizontal direction and 1080 pixels in the vertical direction. On the other hand, the LCD monitor 5B comprises 1280 pixels in the horizontal direction and 1024 pixels in the vertical direction.

Further, the aspect ratio for HDTV display can be selectively set to 4:3, 5:4, or 16:9.

In the present embodiment, as shown in FIG. 14A, in the 4:3 mode, the video processor 4 cuts away 1440×1080 pixels. Furthermore, as shown in FIG. 14B, in the 5:4 mode, the video processor 4 cuts away 1280×1024 pixels.

In the present embodiment, the video processor 4 zooms in the endoscopic image so that it becomes close to the 1440× 1080 or 1280×1024 pixel size in association with the 4:3 or 5:4 mode.

Then, the zoomed-in video signal enables the image to be displayed up to the horizontal size in the display size of the LCD monitor 5B shown in the right of each of FIGS. 14A and 14B (as shown by a shaded part in the display size of the LCD monitor 5B).

In the 16:9 mode, a zooming operation is performed as in the case of the 4:3 mode.

With this process, even if the LCD monitor 5B and HDTV format are used to select from the various aspect ratios for display, the endoscopic image can be prevented from appearing small in the display surface of the LCD monitor 5B.

Figure 15:
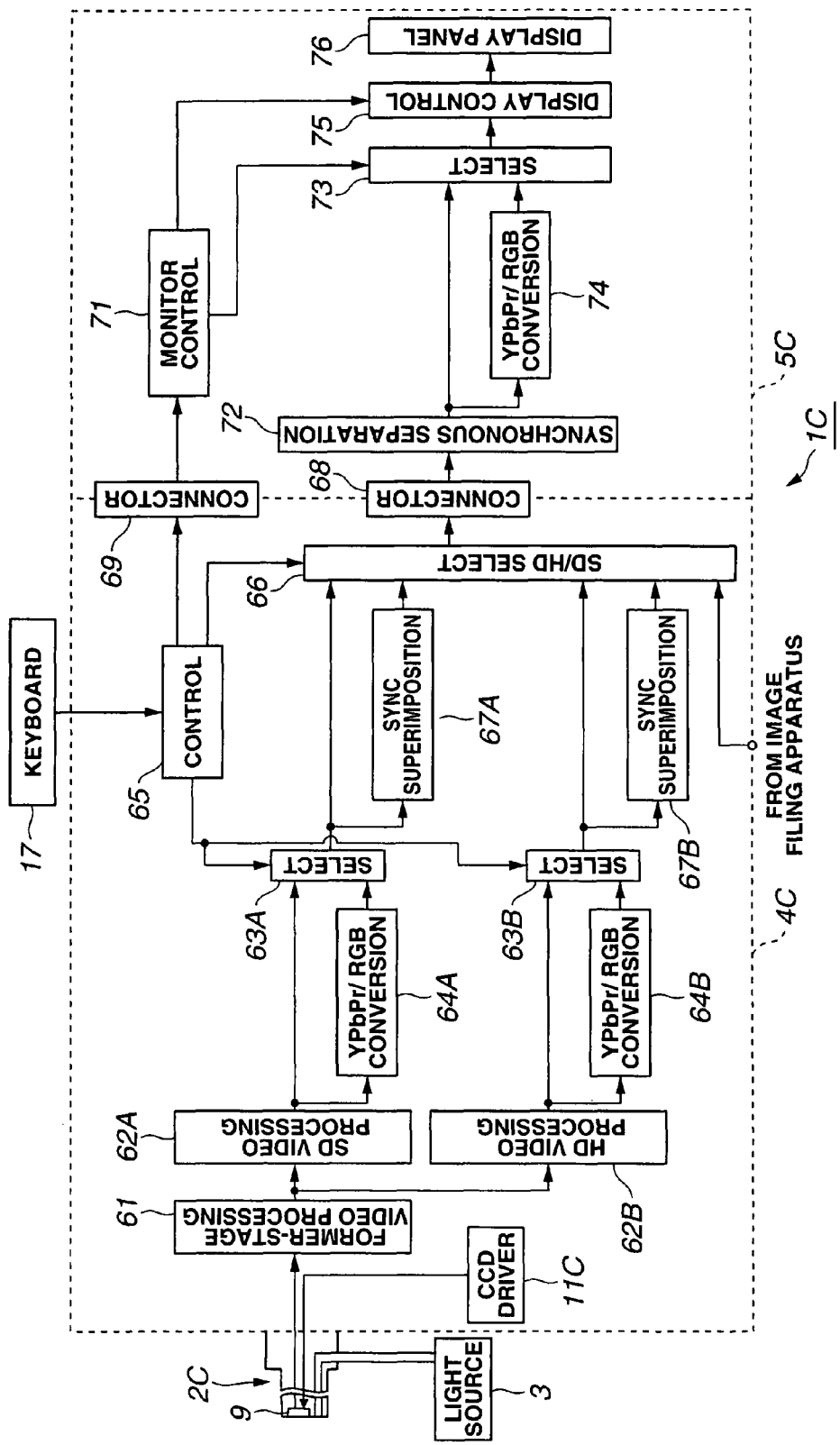
FIG. 15 is a block diagram showing the configuration of an endoscope system in accordance with a first variation.

FIG. 15 shows an endoscope system 1C in accordance with a first variation. The endoscope system 1C is composed of a scope 2C, the light source device 3, a video processor 4C, and a monitor 5C.

The scope 2C corresponds to, for example, the scope 2I in FIG. 1 which does not have, for example, the scope ID generating circuit 13. However, the scope ID detecting circuit 14 may also be provided in the video processor 4C as is the case with the scope 2I in FIG. 1.

A CCD drive signal from the CCD driver 11C in the video processor 4C is applied to the CCD 9, contained in the scope 2C, to read a photoelectrically converted CCD output signal from the CCD 9. The CCD output signal is then input to a former-stage video processing circuit 61 in the video processor 4C for a CDS process and the like. The CCD 9 represents the SDTV-compatible CCD 9A and the HDTV-compatible CCD 9B.

Analog output signals output by the former-stage video processing circuit 61 are input to an SD processing circuit 62A and to an HD processing circuit 62B.

Instruction inputs from the keyboard 17 enable the CCD 9 to be driven and enable the SD processing circuit 62A or HD processing circuit 62B to be selected to process an output signal from the CCD 9.

The SD processing circuit 62A and HD processing circuit 62B executes signal processing in conformity to the SDTV and HDTV formats, respectively.

An output signal from the SD processing circuit 62A is input to a selection circuit 63A and also this circuit 63A via a YPbPr/RGB conversion circuit 64A that converts a YPbPr signal into an RGB signal.

Further, an output signal from the HD processing circuit 62B is input to a selection circuit 63B and also this circuit 63B via a YPbPr/RGB conversion circuit 64B that converts a YPbPr signal into an RGB signal.

The signal selections by the selection circuits 63A and 63B are controlled by control signals from a control circuit 65. Further, the control circuit 65 is connected to the keyboard 17 as an instruction means. An operation of inputting a selection instruction via the keyboard 17 allows the control circuit 65 to perform selective control corresponding to the selection instruction.

An SDTV YPbPr signal or an RGB signal output by the selection circuit 63A is input to an SD/HD selection circuit 66 that executes SD/HD selections. The SDTV YPbPr signal or an RGB signal is also output to the monitor 5C as an external instrument via a SYNC superimposition circuit 67A through an analog video connector 68; the SYNC superimposition circuit 67A executes SYNC superimposition, and the monitor 5C is connected to the analog video connector 68.

Further, an HDTV YPbPr signal or an RGB signal output by the selection circuit 63B is input to the SD/HD selection circuit 66 that executes SD/HD selections. An analog video signal is also output from the analog video connector 68 via a SYNC superimposition circuit 67B that executes SYNC superimposition.

An external video signal from, for example, an image filing apparatus is also input to the SD/HD selection circuit 66. An instruction operation input via the keyboard 17 enables the video signal from the image filing apparatus to be selectively output from a video connector 68.

The control circuit 65 also controls SD/HD selections executed by the SD/HD selection circuit 66. Further, the control circuit 65 is connected to a monitor control circuit 71 in the monitor 5C via a remote connector 69.

In response to a remote control signal from the control circuit 65, which performs control corresponding to an instruction operation input via the keyboard 17, the monitor control circuit 71 controls the sections inside the monitor 5C in conjunction with the video processor 4C.

A video signal input to the monitor 5C through the analog video connector 68 is input to a synchronous separation circuit 72. The synchronous separation circuit 72 then separates a synchronizing signal from the video signal and inputs it to the selection circuit 73. A YPbPr signal is input to the selection circuit 73 via a YPbPr/RGB conversion circuit 74 that converts the YPbPr signal into an RGB signal.

A video signal output by the selection circuit 73 is input to a display panel 76 via a display control circuit 75. Endoscopic images captured by the CCD 9 and the like can thus be displayed on the display panel 76. In accordance with remote control signals from the control circuit 65, the monitor control circuit 71 controls the selection executed by the selection circuit 73 and the display process executed by the display control circuit 75.

For analog video signals, the present variation allows any one of an SDTV and HDTV RGB signals and any one of an SDTV and HDTV YPbPr signals to be output to the monitor 5C via the common video connector 68 in response to an instruction input via the keyboard 17; the SDTV and HDTV RGB signals offer different resolutions, and the SDTV and HDTV YPbPr signals offer different resolutions.

Further, in the monitor 5, the monitor control circuit 71 performs control corresponding to an instruction from the keyboard 17. For example, inputting, via the keyboard 17, an instruction for output of an HDTV YPbPr signal allows the control circuit 65 to control the selection executed by the SD/HD selection circuit 66 so that the HDTV YPbPr signal can be output from the video connector 68.

The YPbPr signal is input to the display control circuit 75 through the synchronous separation circuit 72 and further via the selection circuit 73. The display control circuit 75 subjects the HDTV from the monitor control circuit 71 to a display control process in accordance with information on the aspect ratio or the like (which has been selectively specified via the keyboard 17). An endoscopic image captured by the CCD 9 is thus displayed on the display panel 76 using the HDTV YPbPr signal.

The present variation enables RGB signals as an analog SDTV and HDTV component signals to be selectively output from the common video connector 68. The present variation also enables the selective output of YPbPr signals as an analog SDTV and HDTV luminance/color difference component signals.

The present variation is effective in, for example, simplifying connection operations to improve operability, similarly to Embodiment 1 in FIG. 1.

In the above description, the video connector 68 outputs analog video signals. However, the video connector 68 may output digital video signals. In this case, the present variation exerts almost the same effects. Alternatively, both analog and digital video signals may be output from the video connector 68.

Now, a second variation of the present invention will be described. The second variation comprises a video processor as an endoscope signal processing apparatus comprising a conversion circuit that converts a high-resolution video signal into a low-resolution video signal. As a related prior example, Japanese Patent Laid-Open No. 2004-335 discloses an endoscope apparatus that can output two types of video signals, SDTVs and HDTVs.

Thus outputting two types of video signals offering different resolutions, SDTVs and HDTVs, requires two signal processing circuits to execute respective signal processes. This increases circuit scale and thus costs.

Two circuits are also required each of which generates graphics to be superimposed on endoscopic images. Then, the CPU as control means controls the respective circuits, disadvantageously reducing drawing speed.

Thus, an object of the second variation is to provide an endoscope signal processing apparatus that allows certain components to be shared by both SDTV and HDTV signal processing circuits to reduce the costs and operational burdens on the control means. This endoscope signal processing apparatus is configured as described below.

Figure 16:
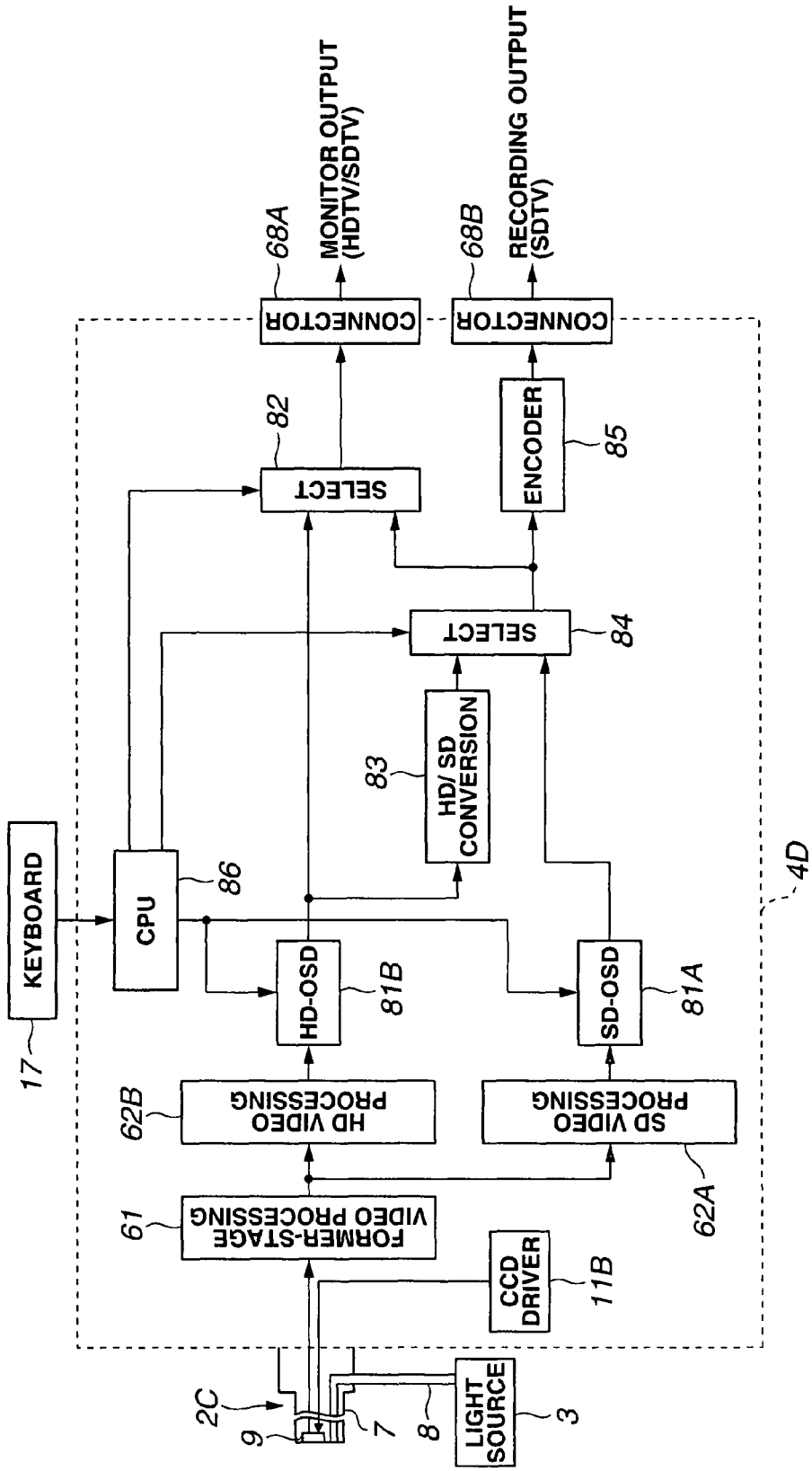
FIG. 16 is a block diagram showing the configuration of a video processor in accordance with a second variation.

FIG. 16 shows a video processor 4D in accordance with the second variation. The video processor 4D outputs HDTV or SDTV video signals to the monitor 5, which displays video signals, and outputs SDTV signals to a recording instrument (specifically, an external instrument other than the monitor 5 which is adapted for the input of SDTV composite video signals).

Separately processing HDTV and SDTV video signals as is the case with Embodiment 1 increases the circuit scale. An object of the present variation is thus to simplify the circuit to reduce its scale and the costs. Another object is to allow the monitor 5 to output SDTVs that enable high quality images to be displayed even during SDTV observations.

The same components as those in FIG. 15 are denoted by the same reference numerals and will not be described below. In the video processor 4D, a CCD output signal is divergently input to the SD video processing circuit 62A and HD video processing circuit 62B via the former-stage video processing circuit 61.

The CCD output signal is subjected to a signal process for the SDTV and a signal process for the HDTV in the SD video processing circuit 62A and HD video processing circuit 62B, respectively. The resulting signals are input to an SD-OSD circuit 81A and an HD-OSD circuit 81B, respectively, which display menus and graphics.

The SD-OSD circuit 81A and HD-OSD circuit 81B generate OSD images such as menu and graphic images which correspond to the SDTV and HDTV, respectively. The OSD images are superimposed on SDTV and HDTV video signals generated from CCD output signals. An output signal from the HD-OSD circuit 81B is output from a component video signal connector 68A via a selection circuit 82 as a monitor output, and is also input to a selection circuit 84 via an HD/SD conversion circuit 83 that downconverts an HDTV video signal into an SDTV video signal offering a lower resolution than the HDTV video signal.

Further, an output signal from the SD-OSD circuit 81A is input to the selection circuit 84. A signal selected by the selection circuit 84 is input to the selection circuit 82 and also output to a recording instrument via an encoder 85 through the (SDTV) composite video signal connector 68B; the encoder 85 converts an SDTV component video signal into a composite video signal.

Further, on the basis of instruction inputs from the keyboard 17, the CPU 86 as control means controls the turning-on and -off of the on-screen process executed by the SD-OSD circuit 81A and HD-OSD circuit 81B as well as the selections executed by the selection circuits 82, 84.

Figures 17, 18:
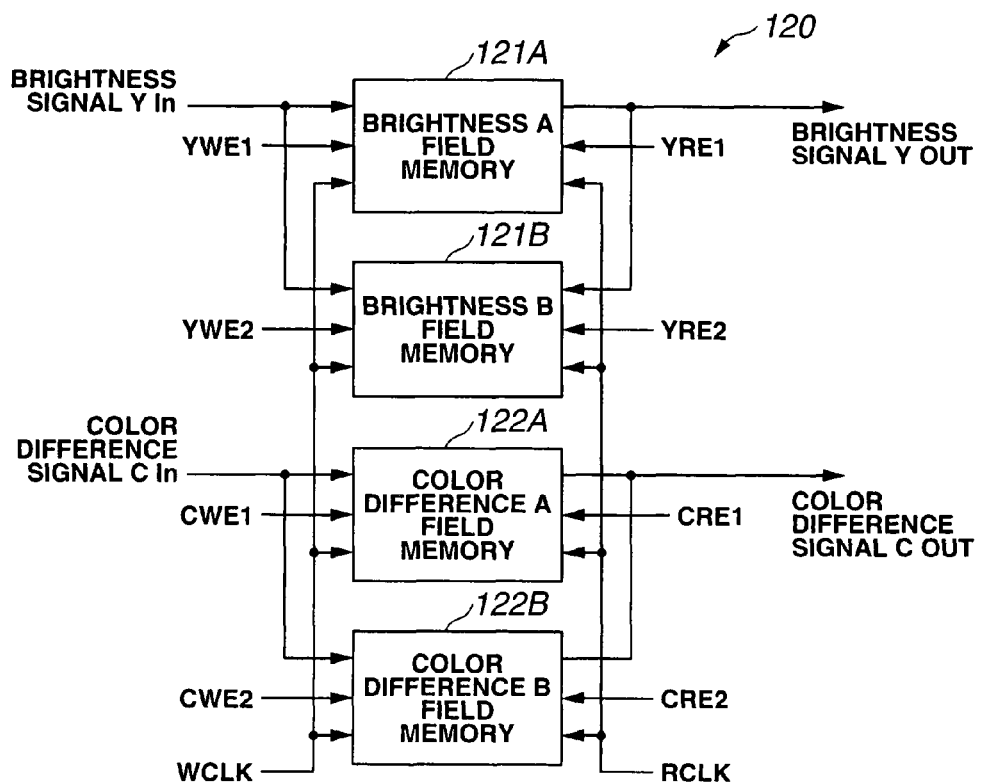
FIG. 17 is a diagram illustrating selection operations performed in the sections shown in FIG. 16 in an SDTV mode and in an HDTV mode.
FIG. 18 is a diagram showing an example of configuration of peripheral section of a memory circuit which executes an HD/SD conversion.

FIG. 17 shows whether each section is used or turned off and how signal selection is executed depending on whether the HDTV or SDTV mode is selected via the keyboard 17.

As shown in FIG. 17, to make observations on the monitor 5 in the HDTV mode, an HDTV is passed through the HD-OSD circuit 81B and then the selection circuit 82 and then output to the monitor 5 via the connector 68A. In this case, the HDTV input to the selection circuit 82 is downconverted into an SDTV by the HD/SD conversion circuit 83. The SDTV is then converted by the encoder 85 into a composite video signal, which is then output to the recording instrument through the connector 68B.

On the other hand, to make observations on the monitor 5 in the SDTV mode, an SDTV is passed through the SD-OSD circuit 81A and then output to the selection circuit 82 via the selection circuit 84. The SDTV is then output to the monitor 5 through the selection circuit 82 via the connector 68A. In this case, the SDTV input to the selection circuit 82 is converted by the encoder 85 into a composite video signal, which is then output to the recording instrument through the connector 68B.

The configuration shown in FIG. 16 has the HDTV signal processing circuit, and the downconvert circuit (HD/SD conversion circuit 83) converts an HDTV video signal from the HDTV signal processing circuit into an SDTV video signal with a different resolution.

Further, such signal switching as shown in FIG. 17 is used to change the method for generating an SDTV video signal to be output to the recording external instrument, depending on the type of signals (HDTV/SDTV) to be observed on the monitor 5. Specifically, to make observations on the monitor 5 in the HDTV mode, the HDTV signal processing circuit and downconvert circuit are operated to output an SDTV resulting from downconversion to the external instrument other than the monitor 5.

On the other hand, to make observations on the monitor 5 in the SDTV mode, only the SDTV signal processing circuit is operated. In this case, since an SDTV image obtained by downconverting an HDTV has a lower image quality than an SDTV, an SDTV generated by the SDTV signal processing circuit is output to the monitor 5 instead of outputting the SDTV output resulting from downconversion to the monitor 5.

In this case, downconversion is not executed, and a composite video signal is output to the external instrument other then the monitor 5 through the encoder 85. This enables a reduction in costs while preventing the image quality from being degraded during observations.

The video processor 4D in accordance with the present variation has a reduced circuit scale and can output HDTVs and high-quality SDTVs to the monitor 5, while outputting SDTVs to an external instrument compatible with SDTV signals.

Further, the video processor 4D in accordance with the present variation has a reduced size and a reduced weight and realizes reduced costs.

Now, description will be given of signal processing required to output SDTVs using the HDTV-compatible CCD 9B. The HDTV-compatible CCD 9B normally outputs HDTV signals but there may be a case where it is desirable to output SDTV signals.

In this case, a simple signal process described below is effective in achieving the above operation. Two methods are available for this signal process.

FIG. 18 shows the configuration of peripheral section of a memory circuit 120 that can be used as, for example, the HD/SD conversion circuit 83 shown in FIG. 16.

A luminance signal Y such as shown in FIG. 18 is written to a luminance A field memory 121A and to a luminance B field memory 121B in accordance with a write clock WCLK, and is read in accordance with a read clock RCLK.

Further, write and read operations on the luminance A field memory 121A are controlled by a write enable signal YWE1 and a read enable signal YRE1, respectively. Further, write and read operations on the luminance B field memory 121B are controlled by a write enable signal YWE2 and a read enable signal YRE2, respectively.

Similarly, a color difference signal C is written to a color difference A field memory 122A and to a color difference B field memory 122B in accordance with the write clock WCLK, and is read in accordance with the read clock RCLK.

Also in this case, similarly to the case of the luminance signal Y write and read operations on the color difference A field memory 122A are controlled by a write enable signal CWE1 and a read enable signal CRE1, respectively. Further, write and read operations on the color difference B field memory 122B are controlled by a write enable signal CWE2 and a read enable signal CRE2, respectively.

Figure 19:
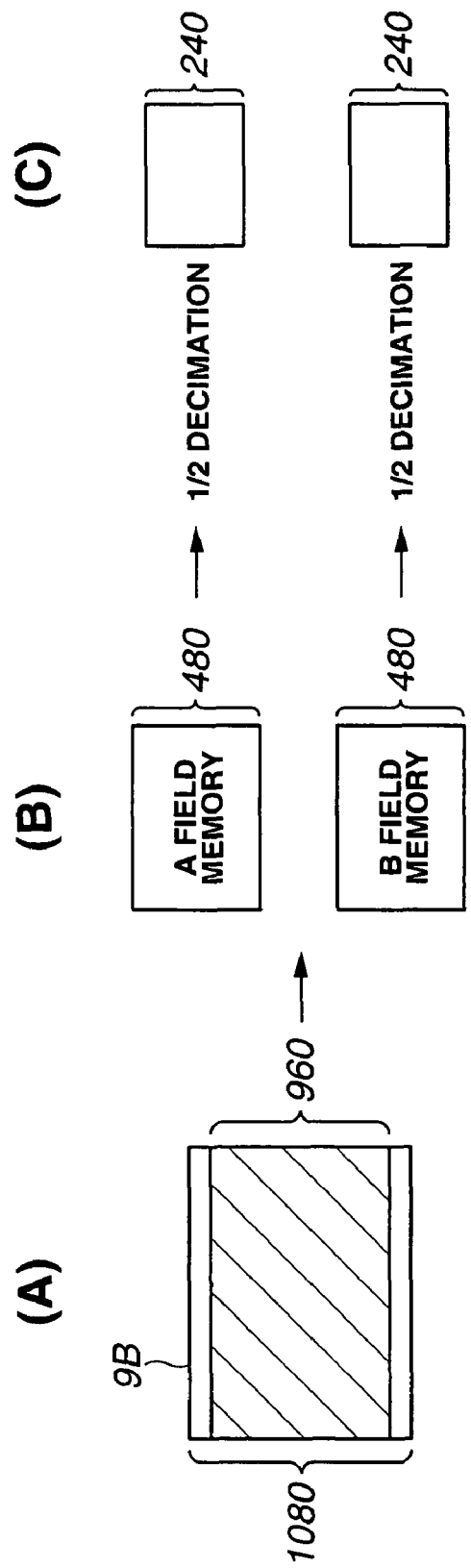
FIG. 19 is a diagram illustrating an operation of converting an HDTV into an SDTV in accordance with a first method.
Figure 20:
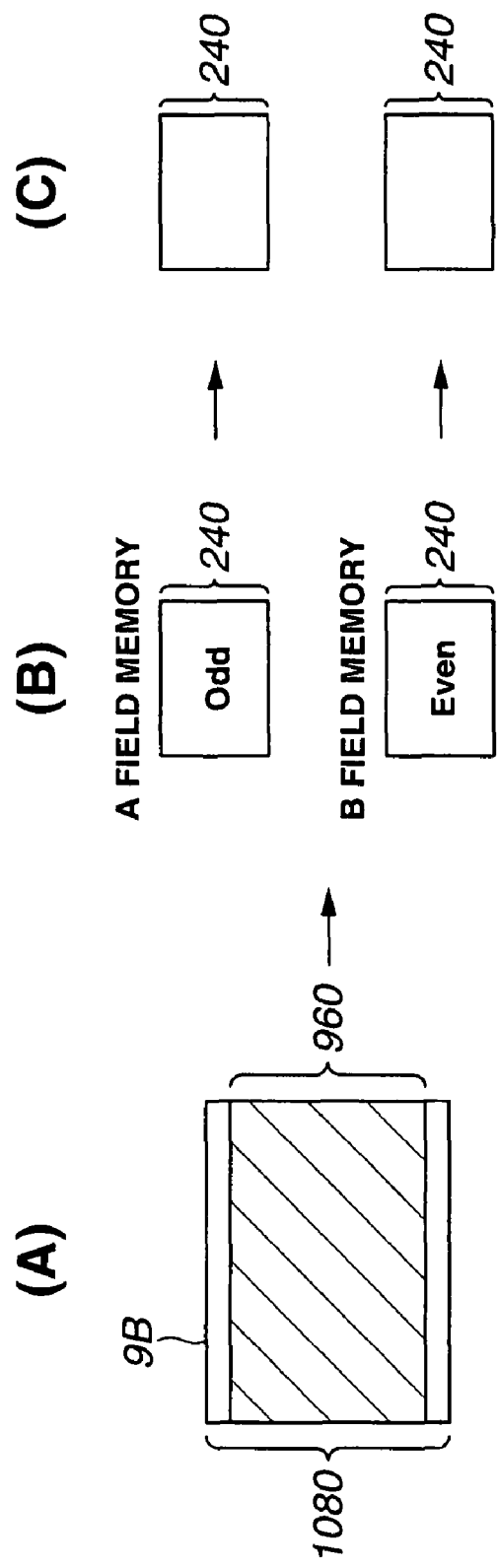
FIG. 20 is a diagram illustrating an operation of converting an HDTV into an SDTV in accordance with a second method.

FIG. 19 is a diagram illustrating an operation of generating a signal to be displayed in the SDTV mode, from an image luminance signal read from the HD-compatible CCD 9B, using the luminance A field memory 121A and luminance B field memory 121B in FIG. 18. A similar operation is used for the color difference signal C. Thus, the description below is directed to the A field memory 121A and B field memory 121B. As shown in FIG. 19A, the HDTV-compatible CCD 9B has 1,080 effective pixels in the vertical direction. The CCD 9B has 1,280 effective pixels in the horizontal direction.

A frame image captured using 960 pixels, corresponding to all the effective pixels in the CCD 9B in the vertical direction except those located at the upper and lower ends, is written to the A field memory 121A and B field memory 121B in an interlacing manner as shown in FIG. 19B; each field memory has a storage capacity of 480 storage pixels in the vertical direction.

As shown in FIG. 19B, the field images written to the interlacing field memories 121A, 121B are read and each decimated to ½ in the vertical and horizontal directions. Then, as shown in FIG. 19C, the field images in the SDTV format which have a pixel size of 240 pixels (pixel lines) in the vertical direction are output for display for each even-numbered field and each odd-numbered field.

This method generates field images from each frame by means of interlacing, allowing even a moving image to be smoothly displayed in accordance with its motion. In other words, a phenomenon is inhibited in which an image moves unnaturally in steps, allowing the image to be smoothly moved.

Now, a second method will be described. This method uses only one of the interlacing field signals for the HDTV-compatible CCD (the other field signal is not used). As shown in FIG. 20A, the method uses the effective pixels in the HDTV-compatible CCD 9B, and uses 960 pixels for the SDTV, that is, all the effective pixels except those located at the upper and lower ends in the vertical direction, as in the case of FIG. 19A.

For one of the interlacing signals read from the CCD 9B in FIG. 20A, odd-numbered lines are written to the A field memory 121A, while even-numbered lines are written to the B field memory 121B as shown in FIG. 20B. In this case, as shown in FIG. 20B, the A field memory 121A and B field memory 121B may have a storage capacity of 240 pixels in the vertical direction.

The field images are thus alternately written to the A field memory 121A and B field memory 121B in an interlacing manner as shown in FIG. 20B. The field images are then read in an interlacing manner and displayed as SDTV interlaced field images as shown in FIG. 20C.

Figure 21:
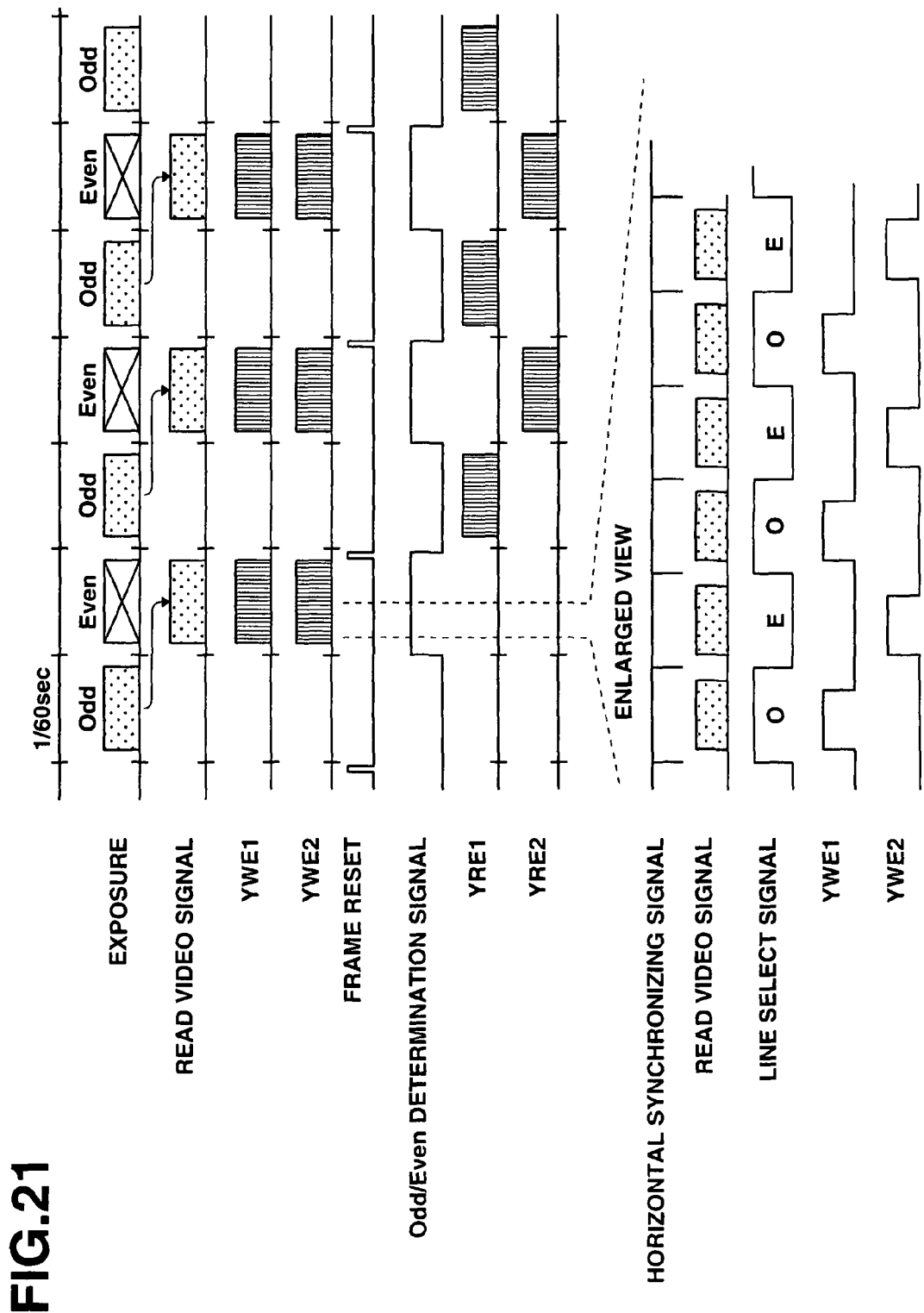
FIG. 21 is a chart of timing for operations from image capturing executed by a CCD through read operations on field memories in the case shown in FIG. 20

FIG. 21 shows a chart of timings for operations from exposure corresponding to this method (image capturing executed by the CCD 9B) to write and read operations on the field memories 121A and 121B. When an image is captured (exposed) by the CCD 9B, for example, only the odd-numbered fields are used as read video signals by means of interlacing. Even-numbered field images are read from the CCD 9B and swept away without being used.

In accordance with the write enable signals YWE1, YWE2, the odd-numbered field video signals are alternately written to the A field memory 121A and B field memory 121B in an interlacing manner. After the write operation, frame resetting is executed.

FIG. 21 shows, at its bottom, an enlarged view of timings at which write operations are alternatively performed on the A field memory 121A and B field memory 121B in an interlacing manner.

Read video signals are read in synchronism with a horizontal synchronizing signal. In accordance with determinations made by a line select signal for the odd and even numbers of the lines, the write enable signals YWE1, YWE2 are alternately set to an enabled state. SDTV interlaced field images are then respectively stored in the A field memory 121A and B field memory 121B alternately set to the enabled state.

Further, whether the fields read from the CCD in an interlacing manner have an odd or even number are determined by an odd/even determination signal. For example, for the odd-numbered fields, the read enable signal YRE1 is applied to the A field memory 121A. For the even-numbered fields, the read enable signal YRE2 is applied to the B field memory 121B.

Thus, for the odd-numbered fields, SDTV format-compatible interlaced field video signals stored in the A field memory 121A are output. For the even-numbered fields, SDTV format-compatible interlaced field video signals stored in the B field memory 121B are output.

The first method is superior in terms of motion. However, in displaying still frame images, the second method can achieve image display with reduced blurring.

Embodiments configured by, for example, combining parts of the above embodiments together also belong to the present invention.

Even an HDTV-compatible CCD having an effective pixel count different from the one described above, 1280×1080, may output SDTV signals using an additional aspect conversion circuit (zoom-in/zoom-out circuit).

Thus, the present embodiment enables plural types of video signals offering different resolutions to be output to the external monitor or the like through the common video signal output connector. This makes it possible to simplify cumbersome connection operations to improve operability.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope signal processing apparatus comprising:
a single endoscope connecting portion to which a first endoscope and a second endoscope is selectively connected;
a first video signal generating circuit for generating a first video signal in association with a first image capturing device which has a first pixel count and which is mounted in the first endoscope connected to the endoscope connecting portion, the first video signal reflecting the first pixel count;
a second video signal generating circuit for generating a second video signal in association with a second image capturing device which has a second pixel count different from the first pixel count and which is mounted in the second endoscope connected to the endoscope connecting portion, the second video signal offering a resolution different from that of the first video signal and reflecting the second pixel count;
a single video signal output connector that selectively outputs one video signal selected from the first video signal and the second video signal to an exterior; and
a single housing in which the endoscope connecting portion, the first and second video signal generating circuits, and the single video signal output connector are provided.

2. The endoscope signal processing apparatus according to claim 1, wherein the single video signal output connector is able to selectively output a standard TV video signal and an HDTV video signal as the first video signal and the second video signal.

3. The endoscope signal processing apparatus according to claim 2, further comprising a conversion circuit for converting the HDTV video signal into the standard TV video signal.

4. The endoscope signal processing apparatus according to claim 2, wherein if the first or second image capturing device is an HDTV image capturing device, the HDTV video signal is generated, and if the first or second image capturing device is a standard video signal image capturing device, the standard TV video signal is generated.

5. The endoscope signal processing apparatus according to claim 1, wherein the single video signal output connector selectively outputs a standard TV video signal and an HDTV video signal as the first video signal and the second video signal, and the video signal output connector is also able to output an analog component video signal or an analog luminance/color difference component signal.

6. The endoscope signal processing apparatus according to claim 1, wherein the single video signal output connector selectively outputs a standard TV video signal and an HDTV video signal as the first video signal and the second video signal, and the video signal output connector is also able to output a digital component video signal, or a digital luminance/color difference component signal, or a serial digital video signal.

7. The endoscope signal processing apparatus according to claim 1, further comprising a connector that outputs a control signal that controls an external instrument when selectively outputting the first video signal and second video signal offering the different resolutions.

8. The endoscope signal processing apparatus according to claim 7, wherein the control signal output from the connector causes control corresponding to a video signal output from the single video signal output connector to be performed on an external instrument connected to the video signal output connector.

9. The endoscope signal processing apparatus according to claim 1, wherein the single video signal output connector outputs the first and second video signals on each of which a synchronizing signal is superimposed, and a synchronizing signal connector is able to output synchronizing signals corresponding to the first and second video signals.

10. The endoscope signal processing apparatus according to claim 1, further comprising an image capturing device identifying circuit for identifying the first and the second endoscopes selectively connected to the endoscope connecting portion to identify the first and second image capturing devices mounted in the first and the second endoscopes, respectively.

11. The endoscope signal processing apparatus according to claim 1, further comprising an instruction device for instructing the single video signal output connector to output one of the first and second video signals.

12. The endoscope signal processing apparatus according to claim 11, wherein the instruction device has a function for specifying an aspect ratio for the one of the video signals output from the single video signal output connector.

13. The endoscope signal processing apparatus according to claim 1, further comprising a PinP image generating circuit for generating a picture-in-picture (PinP) image using one of the first and second video signals.

14. The endoscope signal processing apparatus according to claim 13, wherein the PinP image generating circuit executes a process of PinP-displaying a lower-resolution video signal in a higher-resolution video signal.

15. The endoscope signal processing apparatus according to claim 1, wherein the apparatus has a plurality of the single video signal output connectors for different signal formats.

16. The endoscope signal processing apparatus according to claim 14, wherein the higher-resolution video signal is an HDTV video signal, and the lower-resolution video signal is a standard TV video signal.

17. The endoscope signal processing apparatus according to claim 1, further comprising a conversion circuit for converting one of the first and second video signals which offers a higher resolution into the other offering a lower resolution.

18. The endoscope signal processing apparatus according to claim 17, wherein the conversion circuit is an HDTV video signal/standard TV video signal conversion circuit that converts an HDTV video signal as the higher-resolution video signal into a standard TV video signal as the lower-resolution video signal.

19. The endoscope signal processing apparatus according to claim 18, wherein the HDTV video signal/standard TV video signal conversion circuit generates a standard TV video signal by decimating field video signals read from an HDTV video signal by means of interlacing with a vertically upper end and a vertically lower end of the HDTV video signal partly cut.

20. The endoscope signal processing apparatus according to claim 18, wherein the HDTV video signal/standard TV video signal conversion circuit generates a standard TV video signal from only one of field video signals read from an HDTV video signal by means of interlacing with a vertically upper end and a vertically lower end of the HDTV video signal partly cut.

21. The endoscope signal processing apparatus according to claim 17, wherein the conversion circuit executes a conversion on a video signal having passed through a graphic image superimposition circuit for superimposing a graphic image on the higher-resolution video signal.

22. The endoscope signal processing apparatus according to claim 18, further comprising, in addition to the common video signal output connector, a connector that outputs a standard TV video signal generated by the HDTV video signal/standard TV video signal conversion circuit.

23. The endoscope signal processing apparatus according to claim 1, wherein the single video signal output connector is configured by an analog output connector for outputting one analog video signal selected from the first video signal in analog form and the second video signal in analog form, or a digital output connector for outputting one digital video signal selected from the first video signal in digital form and the second video signal in digital form.

* * * * *